US006410680B1

(12) United States Patent
Kubota

(10) Patent No.: US 6,410,680 B1
(45) Date of Patent: Jun. 25, 2002

(54) DENDRIMER CONSTRUCTS AND METAL COMPLEXES THEREOF HAVING SUPEROXIDE DISMUTASE ACTIVITY

(75) Inventor: Shigeo Kubota, San Francisco, CA (US)

(73) Assignee: DendriMolecular, Inc., San Carlos, CA (US)

( * ) Notice: Subject to any disclaimer, the term of this patent is extended or adjusted under 35 U.S.C. 154(b) by 0 days.

(21) Appl. No.: 09/602,630

(22) Filed: Jun. 21, 2000

(51) Int. Cl.$^7$ .......................... C08G 73/00; A61K 51/00
(52) U.S. Cl. ..................... 528/310; 528/332; 528/363; 528/422; 528/425; 528/482; 424/1.29; 424/1.33
(58) Field of Search ................................. 528/310, 332, 528/363, 422, 425, 482; 424/1.29, 1.33

(56) References Cited

U.S. PATENT DOCUMENTS 5,714,166 A * 2/1998 Tomalia et al. ............. 424/486
6,130,209 A * 10/2000 Newkome et al. ............ 514/51

FOREIGN PATENT DOCUMENTS

JP 61-249388 6/1986

OTHER PUBLICATIONS

A. Archut et al. 1998, Chemical Society Reviews, vol. 27, p. 233.
B. M. Babior, 1997, Brazilian Journal of Medical and Biological Research, vol. 30, pp. 141–155.
L. Balogh et al. 1998, J. Am. Chem. Soc., vol. 120, pp. 7355–7356.
J. S. Choi et al., 2000, J. Am. Chem. Soc., vol. 122, pp. 474–480.
S. A. Comhair et al. 2000 Lancet vol. 9204, p. 624.
R. Ferrari et al. 1989, Pharmacol. Res., vol. 21 suppl. 2, p. 57 ff.
M. Freemantle, 1999, C&EN, Nov., pp. 27–35.
B. Halliwell et al. 1999, Free Radicals in Biology and Medicine, 3d Ed., Oxford, see particularly, pp. 831–32.
B. Halliwell et al. 1999, Free Radicals in Biology and Medicine, 3d Ed., Oxford, see particularly, chapters 9 and 10.
G. Jadot et al. 1995, Clin. Pharmacokinet., vol. 28(1), p. 17 ff.
S. Kawasaki et al. 1993, Eur. Surg. Res., vol. 25(3), p. 129 ff.
T. Kobayashi et al. 1991, Hum. Reprod., vol. 6(7), pp. 987–91.
S. Kubota et al. 1984, Proc. Natl. Acad. Sci. USA, vol. 81, pp. 3283–86.
Y. Miyachi et al. 1987, Jour. Invest. Dermatol., vol. 89(1), pp. 111–12.
J. S. Mok et al. 1998, Br. J. Pharmacol. vol. 124(1), pp. 111–18.
G. R. Newkome et al. 1996, Dendritic Molecules: Concepts, Synthesis, Perspectives, VCH Publishers, Inc. G. R. Newkome et al., supra, section 2.3.3 et seq., and particularly p. 28 ff.
B. Perdereau et al. 1994, Bull. Cancer (Paris), vol. 81(8), pp. 659–69.
D. P. Riley 1999, Chem. Reviews, vol. 99, p. 2573 ff.
D. Salvemini et al. 1999, Science, vol. 286, pp. 304–306 ff.
D. Salvemini et al. 1999, Science, vol. 286, p. 209.
J. R. Stewart et al. 1985, J. Thoracic Cardiovasc. Surg. vol. 90(1), pp. 68–72.
D. Tomalia, et al. 1990, Agnew, Chem Int. Ed. Engl. vol. 29, pp. 138–175.
A. Vaille et al., 1989, Biochem. Pharmacol., vol. 39(2), pp. 247–55.
Wang et al., 2000, J. Am. Chem. Soc., vol. 122, pp. 2193–2199.
Wong et al., 2000, Lancet, vol. 97(6), pp. 2886–2891.
Zhao, et al., 1998, J. Am. Chem. Soc., vol. 120, pp. 4877–4878.

* cited by examiner

*Primary Examiner*—James J. Seidleck
*Assistant Examiner*—Olga Asinovsky
(74) *Attorney, Agent, or Firm*—Bill Kennedy; Haynes Beffel & Wolfeld LLP

(57) ABSTRACT

A metal-dendrimer complex in which the metal active site is deep within the three-dimensional dendrimer construct, has superoxide dismutase-like activity. In particular embodiments the complex is a copper(II)-dendrimer complex and the dendrimer construct is a dendritic polypeptide, and the copper(II) is complexed with imidazole groups provided by histidine side groups within the dendritic construct. The dendrimer construct has a generally globular shape, and the branched chains nearer the surface are sufficiently densely packed to restrict the movement of larger biomolecules into the dendritic construct toward the metal active sites. Smaller molecules such as the superoxide anion ($O_2^-$) move freely from the milieu into the dendritic complex and to the metal active sites, where the dismutation of superoxide to hydrogen peroxide is effected; and smaller molecules such as hydrogen peroxide move freely out from the dendritic complex to the milieu.

Also, a method for treating or preventing a disease condition associated with oxidative stress includes administering such a metal-dendrimer complex to a subject in need of treatment, in a form and by a route of administration suitable for bringing the complex to the site of the condition.

23 Claims, 8 Drawing Sheets

DENDRIMER CONSTRUCTS AND METAL COMPLEXES THEREOF HAVING SUPEROXIDE DISMUTASE ACTIVITY

FIELD OF THE INVENTION

This invention relates to treating oxidative stress and, particularly, to treating disease conditions associated with a presence of superoxide and of reactive chemical species derived from superoxide.

BACKGROUND

The oxygen radicals (including for example "superoxide", $O_2^{\cdot-}$; hydroxyl radical, $OH^{\cdot}$) and some non-radical derivatives of $O_2$ (including for example hydrogen peroxide, $H_2O_2$) are commonly known as reactive oxygen species ["ROS"]. During electron transport in redox reactions in all living organisms the reduction of molecular oxygen by a single electron generates the reactive oxy-radical, i.e., the superoxide anion ($O_2^{\cdot-}$). ROS, including superoxide and chemical species derived from it, can be damaging to living systems. In healthy aerobic organisms, production of ROS (and of reactive nitrogen species ["RNS"]) is balanced by antioxidant defenses. The balance is imperfect, however, and some ROS- and RNS-mediated damage is ongoing to greater or lesser degrees. In healthy organisms, damaged biomolecules are continually repaired or replaced.

A serious imbalance that arises between production of ROS/RNS and the antioxidant defenses is referred to as "oxidative stress", and significant oxidative damage can be caused by oxidative stress. Oxidative stress can result from diminished antioxidants (for example by depletion or underproduction of antioxidants as a result of dietary insufficiency or genetically associated metabolic deficiency), or from increased production of ROS/RNS (for example by exposure to elevated $O_2$ or by metabolism of toxins or by excessive activation of ROS/RNS-producing pathways resulting from inflammatory disease processes).

Oxidative stress is associated with a wide variety of disease conditions. In some instances oxidative stress is a primary cause of the disease condition (e.g., radiation-induced damage, some cancers, some drug side effects, and sometimes atherosclerosis and hypertension); or probably is a primary cause (e.g., Vitamin E deficiency and Selenium deficiency). In other instances oxidative stress is secondary, but may contribute significantly to pathology (e.g., atherosclerosis, rheumatoid arthritis, and inflammatory bowel disease, and possibly a significant number of other diseases).

Under normal circumstances in cytosol or on extracellular surfaces the superoxide radical is consumed by superoxide dismutases (SODs). SOD enzymes are oxoreductases (EC 1.1.5.1.1) that contain copper, iron, or manganese ion in the active site and catalyze the dismutation of $O_2^{\cdot-}$ radicals to molecular oxygen and hydrogen peroxide, which is further converted to molecular oxygen and water by catalase. Many mammalian diseases may be characterized as conditions in which the body fails to contain an overproduction of the $O_2^{\cdot-}$ radical and of the more harmfully reactive $O^{\cdot}$. radical which is consequently derived through Fenton chemistry between reduced metal ions ($Cu^+$, $Fe^{2+}$) and hydrogen peroxide.

In certain metabolic processes, the production of $O_2^{\cdot-}$ is enhanced, resulting in tissue injury and disease. Examples of such oxidative stress-related diseases include perfusion injury, such as that which occurs after acute myocardial infarction or stroke, inflammatory processes such as arthritis, inflammatory bowel conditions and stomach ulcers.

Considerable effort has been directed toward developing pharmaceuticals that might be therapeutically useful in ameliorating tissue injury and disease associated with oxidative stress. In one general approach, an excess of reactive oxygen species would be corrected by administering an agent that would produce increased superoxide dismutase activity where oxidative stress is either underway or likely to occur. Attempts have been made, for example, to administer a superoxide dismutase (typically, a CuZn-SOD) enzyme of animal origin to a subject in need of treatment. The SOD may be used in the native state, but some have proposed modifying it in some manner, such as by treatment with albumin (see, e.g., L. G. Cleland et al. 1979, *Arthritis Rheum.*, Vol. 22, p. 559) polyethylene glycol (see, e.g., J. M. McCord et al. 1979, in, "Excerpta Medica", *Ciba Foundation Symposium*, Vol. 65, pp. 343–60), ficoll (see, e.g., W. F. Petrone et al. 1980, *Proc. Nat'l. Acad. Sci. USA*, Vol. 77, pp. 1159–63), polyalkylene glycol (see, e.g., Japanese Patent No. 61-249388 (Ajinomoto Co., 1985)) or liposome (see, e.g., A. M. Michelson 1982, *Agents Action*, Vol. 11, pp. 179–210). Modification of SOD enzymes may provide advantages for their use as drugs. A suitably modified SOD may, for example, have longer lifetime in vivo, or may have reduced toxicity as compared to the native enzyme, or may have reduced immunogenicity (see, e.g., A. Abuchowski et al. 1978, *Recl. Trav. Chim. Pays-Bas*, Vol. 97, pp. 293–95). However, such modified enzymes may be costly, and the modifications may reduce their effective catalytic activity.

Others have proposed administering synthetic lower molecular weight metal complexes, and a variety of small-molecule SOD "mimics" have been developed and tested for pharmaceutical efficacy (see, e.g., B. Halliwell et al. 1999, *Free Radicals in Biology and Medicine*, 3d Ed., Oxford, see particularly, pp. 831–32). Where such SOD mimics employ copper or iron as the metal, however, they may generate highly reactive OHM radicals, which can rapidly interact with surrounding living materials, resulting in tissue injury and aggravation of the disease state.

SUMMARY

In one general aspect the invention features a dendrimer construct having a core and two or more branched arms projecting outwardly from the core. The arms include internal branched units and terminal moieties; the terminal moieties constitute an outermost surface of the dendrimer construct. The arms include at least one metal ion binding site enclosed within the outermost surface. The outermost surface of the dendrimer construct is sufficiently densely packed to restrict the movement of larger molecules from the milieu into the dendritic construct, and the surface is sufficiently porous to permit free movement of smaller molecules from the milieu into the dendrimer construct and to the metal ion binding site and out from the dendrimer construct to the milieu.

In another general aspect the invention features a metal-dendrimer complex in which a metal active site is enclosed within the surface of the dendrimer construct. The dendrimer construct includes a core and two or more branched arms projecting outwardly from the core. The arms include internal branched units and terminal moieties; the terminal moieties constitute the outer surface of the dendrimer construct. The arms include at least one metal ion binding site associated with one or more internal branched units and enclosed within the outermost surface, and a metal ion is complexed at the metal ion binding site to form the metal active site. The outermost surface of the dendrimer construct is sufficiently densely packed to restrict the movement of larger molecules from the milieu into the dendritic construct Smaller molecules such as the superoxide anion ($O_2^-$) move freely from the milieu into the dendrimer construct and to the metal active site, where the dismutation of superoxide to hydrogen peroxide is effected; and smaller molecules such as hydrogen peroxide move freely out from the dendrimer construct to the milieu.

In some embodiments the metal ion in the complex is an ion of a transition metal such as copper, manganese, or iron; in particular embodiments the metal ion is an ion of copper, particularly copper(II); or is an ion of iron, particularly iron(III).

In some embodiments the dendrimer construct results from sequential monomer addition in a divergent synthesis, beginning from a core and constructing the branched arms by proceeding outwardly through successive generations (the core being the zeros$^{th}$ generation). One mode of such divergent synthesis proceeds by sequential addition of monomers using a protection-deprotection scheme. The core may have two (divalent), three (trivalent), four (tetravalent) or more reactive moieties, providing points of attachment for, respectively, two, three, four or more branched arms; usually the core is divalent or trivalent.

A The monomers or branching units making up the arms may be 1→2 branching or 1→3 branching. The dendrimer construct may have all structurally similar arms, and each arm may contain similar repeat internal branch units (except for one or more branch units with which the ion binding site is associated); or each arm may contain dissimilar internal branch units. Or, the dendrimer construct may have structurally different arms, each having either similar or dissimilar internal branch units or terminal moieties.

Preferred internal branch units, at least in the vicinity of metal active sites, include structures that are less likely to be degraded by the presence of the superoxide anion ($O_2^-$) or of its derivatives such as the highly reactive $OH^{\cdot}$ radical which may exist transiently near the metal reactive site, or hydrogen peroxide.

In some embodiments the dendrimer construct is a dendritic polypeptide or a dendritic polyamidoamine. Suitable monomers include any of various L-, D-, or DL-α-amino acids carrying functional groups in the side chains R, where R has the general formula $(CH_2)_nNH_2$, where n=1–7; or the general formula $(CH_2)_nCOOH$, where n=1–7.

In some embodiments the metal ion is complexed with imidazole groups provided by L-histidine within the dendrimer construct Particular such embodiments include dendrimer constructs having 1,4-diaminobutane ["DAB"] as a core and having L-lysine ["K"] as a monomer for each generation except that generation in which L-histidine ["H"] is used to provide imidazole coordination sites for copper ions. In some such embodiments 16 histidine residues are provided and, accordingly, histidine is employed as the monomer at the fourth generation; these include the $D_6$ construct $(DAB)K_2K_4K_8H_{16}K_{16}K_{32}$, the $D_7$ construct $(DAB)K_2K_4K_8H_{16}K_{16}K_{32}K_{64}$, and the $D_8$ construct $(DAB)K_2K_4K_8H_{16}K_{16}K_{32}K_{64}K_{128}$. Where, as in these embodiments, 16 imidazole groups are provided, the number of copper(II) ions that may be complexed in each molecule may be in the range from as few as 1 to as many as 4, more usually from 1 to 3 or from 1 to 2. In some embodiments the N(1) of the imidazole group is alkylated with an iodoalkane having the general formula $I(CH_2)_nH$(n=1–8). (See, A. Noordam et al. 1978, Recl. Trav. Chim. Pays-Bas, Vol 97, pp. 293–95.)

In another general aspect the invention features a method for treating or preventing a disease condition associated with oxidative stress, by administering to a subject in need of treatment a metal-dendrimer complex according to the invention, in a form and by a route of administration suitable for bringing the complex to the site of the condition. A disease condition associated with oxidative stress, as that expression is used herein, is one in which oxidative stress is a primary cause or in which oxidative stress is secondary to the condition but contributes significantly to disease pathology.

In some embodiments the disease condition to be treated is an oxidative stress associated disease of the gastrointestinal tract and the metal-dendrimer complex is administered orally for topical treatment within the gastrointestinal lumem. As will be appreciated, movement of molecules across the mucosa can be influenced by molecular size as well as various other properties, and absorption can be effected differently in different regions of the digestive tract. See, e.g., McMartin et al. 1987, Jour. Pharm. Sci, Vol. 76, pages 535 ff.; Peters et al. 1987, Jour. Pharm. Si., Vol. 76, pages 857 ff. A preferred metal-dendrimer complex for topical treatment in the digestive tract has a higher molecular weight, usually in the range about 50 kd to about 100 kd or greater, so that absorption of the complex across the digestive tract mucosa, and clearance of the complex through the kidneys, will be limited. In some embodiments a metal-dendrimer complex for treatment in the digestive tract has a molecular weight in the range about 50 daltons to about 100 daltons.

The water-soluble metal-dendrimer complexes according to the invention can be useful in treatment of any of a variety of disease conditions associated with oxidative stress. For example, a Copper(II)-dendritic peptide complex having molecular size in the range greater than about 50 kd can also be administered rectally, or by intravenous, intraperitoneal, intramuscular, or subcutaneous injection, for treatment of damage associated with oxidative stress in the digestive tract.

The dendrimer construct will not be a substrate for enzymatic degradation Moieties in the outermost tiers, on the surface of the dendritic construct, can be modified to facilitate affinity of the complex to cell surfaces or tissues, and particular modifications can be used to provide affinity for selected types of cells or tissues. The surface of the dendritic construct can be modified, for example by use of agents such as polyethylene glycol (see, e.g., C. O. Beauchamp et al. 1978, Anal. Biochem., Vol. 131, pp. 25–33) to reduce inununogenicity of the complex; or, for example, by use of alkyl groups to facilitate affinity of the construct to cell surfaces or tissues or to facilitate permeability of the construct across membrane bilayers; or, for example, by conjugation to the dendrimer construct of selected cationic peptide fragments, which have a high aiffity for heparin-like proteoglycans in targeted cells or tissues (see, e.g., M. Inoue et al 1991, Jour. Biol. Chem., Vol. 266, pp. 16409–14), to promote accumulation of the complexes at one or more targeted disease sites. The molecular size of the dendrimer complex can be readily controlled Interaction of proteins or protein fragments with the surface of the dendrimer construct is expected not to substantially alter or destroy the tertiary structure of metal active site. Even where a surface-modified metal-dendrimer complex according to the invention is employed, small molecules such as the $O_2^-$ radical can diffuse relatively unimpeded to the active site, where they participate in the redox reaction. The metal active site is situated deeply within the dendrimer construct. The extremely reactive and harmful hydroxyl radical ($OH^{\cdot}$), which is an expected product of Fenton chemistry at the active site, is rapidly converted to hydrogen peroxide before it can leave the dendrimer complex to the surrounding milieu because the hydroxyl radical has a short life time (~70 ns; I. Saito et al. 1990, *Chemistry of Active Oxygens*, chapter 1, p. 4, M. Misono, ed., Chemical Review No.7, Chemical Society of Japan, Tokyo (in Japanese)) and the rate constant k for the dismutation reaction $OH^\cdot + OH^\cdot \rightarrow H_2O_2$ is extremely high ($k=5\times10^{-9}$ $M^{-1}S^{-1}$; B. Halliwell et al., supra, p. 57).

The invention will now be described in further detail, with reference to the drawings.

DETAILED DESCRIPTION

Figure 1:
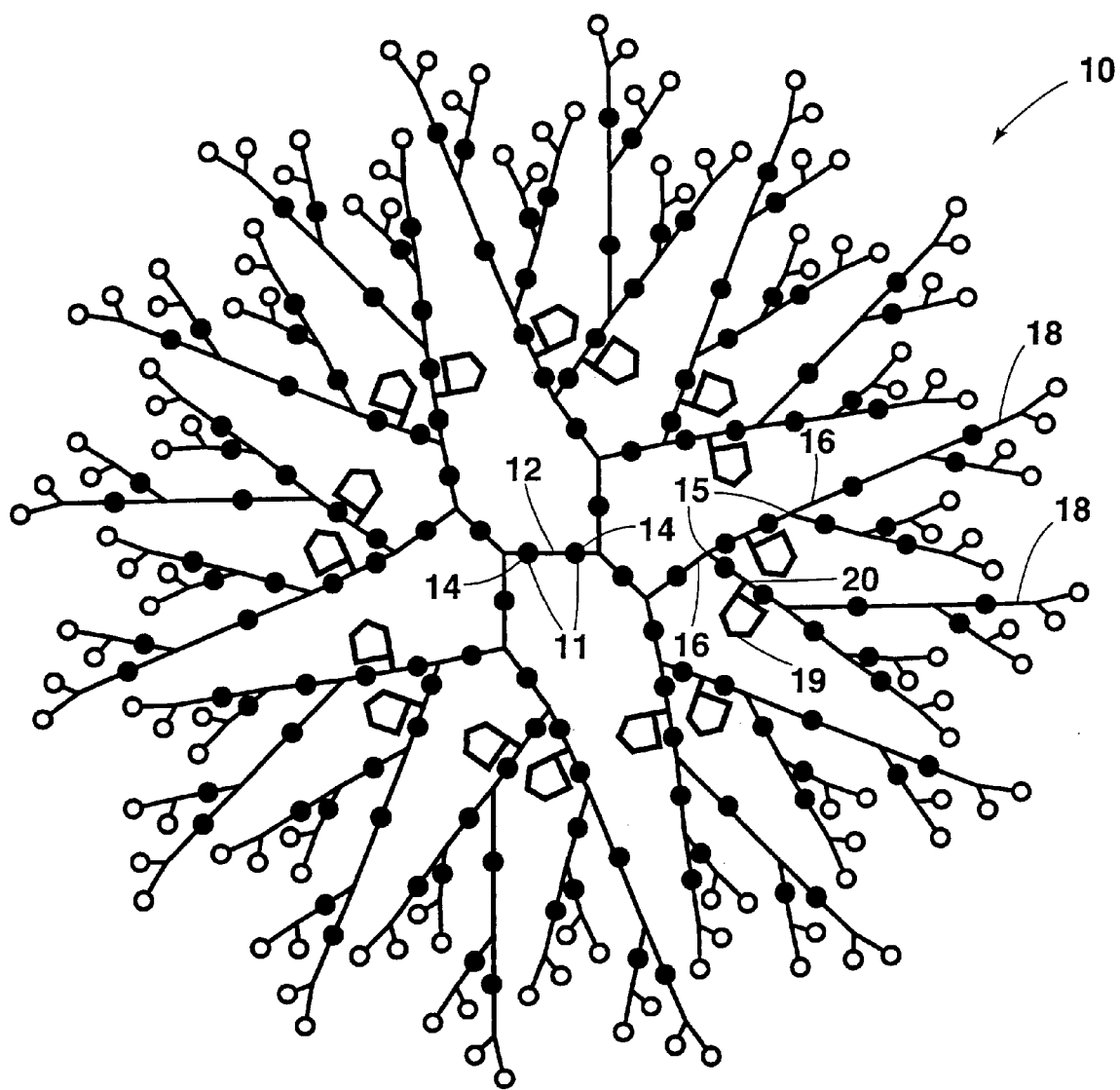
FIG. 1 is a two-dimensional schematic representation of the structure of an example of a host seventh generation dendrimer (D7) according to the invention, constructed as a L-lysine-based dendritic polypeptide having a 1,4-diaminobutane core and L-histidyl residues at the $4^{th}$ generation, namely: $D_7$: (1,4-diaminobutyl)$(Lys)_2(Lys)_4(Lys)_8(His)_{16}(Lys)_{16}(Lys)_{32}(Lys)_{64}$. The open circles represent free amino groups, and the filled circles represent amide groups.

Structure.

Dendrimer constructs according to the invention have two or more branched arms projecting outwardly from a core. The arms include internal branched units and terminal moieties; the terminal moieties constitute an outermost surface of the dendrimer construct. The arms include at least one metal ion binding site enclosed within the outer surface. The terminal moieties near the outer surface of the dendrimer construct are sufficiently densely packed to restrict the movement of larger molecules from the milieu into the dendritic construct and the surface is sufficiently porous to permit free movement of smaller molecules from the milieu into the dendrimer construct and to the metal ion binding site and out from the dendrimer construct to the milieu.

In another general aspect the invention features a metal-dendrimer complex in which a metal active site is enclosed within the surface of the dendrimer construct. The dendrimer construct includes a core and two or more branched arms projecting outwardly from the core. The arms include internal branched units and terminal moieties; the terminal moieties constitute the outermost surface of the dendrimer construct. The arms include at least one metal ion binding site associated with one or more internal branched units and enclosed within the outer surface, and a metal ion is complexed at the metal ion binding site to form the metal active site. The terminal moieties on the outermost surface of the dendrimer construct are sufficiently densely packed to restrict the movement of larger molecules from the milieu into the dendritic construct. Smaller molecules such as the superoxide anion ($O_2^-$) move freely from the milieu into the dendrimer construct and to the metal active site, where the dismutation of superoxide to hydrogen peroxide is effected; and smaller molecules such as hydrogen peroxide move freely out from the dendrimer construct to the milieu.

Any of a variety of dendrimer constructs can be suitable according to the invention. An overview of dendrimer structures and methods for constructing them is presented, for example, in G. R. Newkome et al. 1996, *Dendritic Molecules: Concepts, Synthesis, Perspectives*, VCH Publishers, Inc. This and all other publications cited in this application are hereby incorporated herein by reference in their entirety.

In some embodiments the dendrimer construct results from sequential monomer addition in a divergent synthesis, beginning from a core and constructing the branched arms by proceeding outwardly through successive generations (the core being the zero$^{th}$ generation). One mode of such divergent synthesis proceeds by sequential addition of monomers using a protection-deprotection scheme. The core may have two (divalent), three (trivalent), four (tetravalent) or more reactive moieties, providing points of attachment for, respectively, two, three, four or more branched arms; usually the core is divalent or trivalent.

Examples of suitable cores include alkylamines such as diaminopropane, diaminobutane and tris(2-aminoethyl) amine. In some particular dendrimer constructs according to the invention the core is a diaminoalkane such as 1,2-diaminoethane, 1,3-diaminopropane, 1,2-diaminopropane, 1,2-diamino-3-methylpropane, 1,4-diaminobutane, 1,3-diaminobutane, 1,2-diaminobutane, 1,5-diaminopentane, and the like. In others the core is a cyclic amino compound, such as a diamino cyclohexane, including 1,4-diaminocyclohexane and various positional isomers thereof. In still others the core is a triamine molecule such as 1,4,7-triazacyclononane or 1,5,9-triazacyclododecane. 1,2-diaminobutane, 1,5-diaminopentane, and the like. In others the core is a cyclic amino compound, such as a diamino cyclohexane, including 1,4-diaminocyclohexane and various positional isomers thereof In still others the core is a triamine molecule such as 1,4,7-triazacyclononane or 1,5,9-triazacyclododecane.

The monomers or branching units making up the arms may be 1→2 branching or 1→3 branching. The dendrimer construct may have all structurally similar arms, and each arm may contain similar repeat internal branch units (except for one or more branch units with which the ion binding site is associated); or each arm may contain dissimilar internal branch units. Or, the dendrimer construct may have structurally different arms, each having either similar or dissimilar internal branch units or terminal moieties.

Preferred internal branch units, at least in the vicinity of metal active sites, include structures that are less likely to be degraded by the presence of the superoxide anion ($O_2^{·-}$) or of its derivatives such as the highly reactive OH·radical, which may exist transiently near the metal reactive site, or hydrogen peroxide.

In general, the molecule of the metal ion-dendrimer complexes of the invention has a globular form. Depending upon whether the arms are more or less similar, and upon the shapes of the internal branching units and the terminal moieties, the shape of the molecule may more or less approximate a sphere. Such a molecule typically includes a more or less open spatial structure having dynamic pockets and channels, and may be characterized as having some degree of "porosity" for molecules having various dimensions. Theoretical modeling approaches can be employed for estimating the porosity of a proposed structure (see, e.g., G. R Newkome et al., supra, section 2.3.3 et seq., and particularly pages 28 ff). The dendritic constructs according to the invention have a porosity sufficient large to permit access by superoxide radical from the milieu to the metal active site within the structure, and to permit movement of hydrogen peroxide away from the metal active site out from the structure to the milieu; yet sufficiently small to substantially prevent access by larger molecules, particularly biomolecules, that may interfere with the movement of superoxide radical and its products to and from the metal active site, or may interfere with the SOD activity at the metal active site. amino acids carrying functional groups in the side chains R, where R has the general formula $(CH_2)_nNH_2$, where n=1–7; or the general formula $(CH_n)_nCOOH$, where n=1–7.

Referring now to FIG. 1, there is shown by way of example the schematic two-dimensional structure of a dendrimer construct for use in forming metal-dendrimer complexes of the invention. As will be appreciated, the bonds of the molecule will, in a solvent, flex and rotate so that the molecule in its three-dimensional configuration assumes a generally globular radially symmetrical form. This dendrimer construct 10 has a core 12 with two reactive moieties 11 and thus having two similar multiply branching arms 14. The arms 14 include internal branched units, e.g., 16, and terminal moieties, e.g., 18; the terminal moieties constitute an outermost surface of the dendrimer construct The internal branched units 16 in this example are 1→2 branching, as the branch points, e.g., 15, illustrate. In each of the arms, metal-coordination moieties, e.g., 19 are associated with the internal branched units, e.g., 20 at the fourth generation; accordingly, there are 8 metal-coordination moieties associated with each arm, or 16 metal-coordination moieties enclosed within the entire construct. Except for those internal units, e.g., 20, with which the metal-ion coordinating moieties, e.g., 19, are associated, the internal branched units are similar. In its three-dimensional configuration, having 64 terminal branching units, the outermost surface of this dendrimer construct is sufficiently densely packed to restrict the movement of larger molecules from the milieu into the dendritic construct and the surface is sufficiently porous to permit free movement of smaller molecules from the milieu into the dendrimer construct and to the metal ion binding site and out from the dendrimer construct to the milieu.

The metal ion in the complex is an ion of a metal such as copper, manganese, or iron; in particular embodiments the metal ion is an ion of copper, particularly copper(II); or is an ion of iron, particularly iron(III). The metal ion binding site may be constructed using any of a variety of moieties suitable for complexing copper or manganese or iron. For copper complexes, particularly, the metal ion is complexed with imidazole groups provided by histidine within the dendrimer construct.

Examples of such complexes, described in more detail below, include dendrimer constructs having 1,4-diaminobutane ["DAB"] as a core and having L-lysine ["K"] as a monomer for each generation except that generation in which L-histidine ["H"] is used to provide imidazole coordination sites for copper ions. In some such embodiments 16 histidyl residues are provided and, accordingly, histidine is employed as the monomer at the fourth generation; these include the $D_6$ construct $(DAB)K_2K_4K_8H_{16}K_{16}K_{32}$, the $D_7$ construct $(DAB)K_2K_4K_8H_{16}K_{16}K_{32}K_{64}$, and the $D_8$ construct $(DAB)K_2K_4K_8H_{16}K_{16}K_{32}K_{64}K_{128}$. Where, as in these embodiments, 16 imidazole groups are provided, the number of copper(II) ions that may be complexed in each molecule may be in the range from as few as 1 to as many as 4, more usually from 1 to 3 or from 1 to 2. In some embodiments the N(1) of the imidazole group is alkylated with an iodoalkane having the general formula $I(CH_2)_nH$ (n=1–8) (A. Noordam et al., supra).

Synthesis.

The dendrimer constructs according to the invention can be synthesized by any of a variety of techniques known to synthetic chemists. Techniques for synthesis of dendrimer constructs are known (for an overview see, e.g., G. R Newkome et al. 1996, *Dendritic Molecules*, VCH (FRG)).

In one technique the dendrimer is constructed by an iterative divergent process, beginning with a core initiator and sequentially adding tiers of monomers, employing an iterative protection-deprotection scheme. The metal active site is constructed as a metal ion-complexing structure in an inner tier. Depending on what materials are used in construction of the dendrimers, the resulting metal ion- (e.g., copper(II)-) dendrimer complex can mimic SOD and certain properties of micelles, liposomes, and biomolecules such as proteins.

Referring again to FIG. 1, in an exemplary embodiment this dendrimer construct can be a L-lysine-based dendritic polypeptide having 1,4-diaminobutane as a core 12 and having histidyl residues 20 in the $4^{th}$ generation. Prediction of the three-dimensional structure suggests that the 16 imidazole moieties 19 provided by histidyl residues in the $4^{th}$ would be expected to form a cluster for coordination with $Cu^{2+}$ions. The outermost tier is densely populated with branched terminal chains and would be expected to hinder any intrusion of large molecules such as proteins into the dendrimer structure to the copper-active sites.

The stability of a copper(II) complex using histidine residues as coordination structures can be improved by modification of the histidine residues. For example, the imidazole group can be alkylated at the N(1) position with an iodoalkane having the general formula $I(CH_2)_nH$ (A. Noordam et al., supra), where n=1–8. Such alkylation can enhance the stability constant, improving SOD activity of the Cu(II)-chelate complexes over a range of pH as wide as pH 1.3 to 9.

Where metal ions other than copper are to be complexed, other coordination structures may be employed at the complexing sites by insertion of suitable complexing moieties into the dendrimer construct For example, ions of Fe or M can be chelated to a linear or a macrocyclic ligand such as desferrioxamine (see, e.g., B. Halliwell et al., supra, chapter 10, particularly p. 843), a porphyrin, or bis (cyclohexylpyridine). Desferrioxamine can be attached to the carboxyl group by conventional peptide chemistry. Attachment of macrocyclic ligands can be carried out following functionalization of rings.

Metal-dendrimer complexes having Fe(III) can be constructed using a derivative of the TPAA molecule, which is reported to act as an SOD mimic when complexed with the Fe(III) ion. (See, e.g., T. Nagano et al. 1989, *Jour. Biol Chem.*, Vol. 264, pages 9243 ff.; T. Nagano et al. 1991, *Free Radical Research Comm.* 1991, Vol. 12/13, pages 221 ff.; D. P. Riley 1999, *Chem. Reviews*, Vol. 99, pages 2573 ff.)

EXAMPLES

In these examples, synthesis of dendritic polypeptides and their copper(II) complexes is described in detail, and their SOD-mimicking activity in vitro is demonstrated.

Reagents and other materials used in the Examples were obtained as follows. N,N'-Bis(tert-butoxycarbonyl)-L-lysine was prepared from L-lysine monohydrochloride (Aldrich, cat. L460-5) and di-tert-butyl dicarbonate (Chem Impex International, cat. 00128) in the standard procedure. L-Histidine (cat. 15,168-8), N-hydroxysuccinimide (cat 13,067-2), ammonium formate (cat. 15,626-4) and copper (II) chloride (99.999% pure, cat. 20,203-1) and all organic solvents of reagent grade were obtained from Aldrich. Trifluoroacetic acid (Aldrich. cat. 30,203-1) was spectrophotometric grade of more than 99% pure. N,N-dicyclohexylcarbodiimide (cat 00114) and N-hydroxy-5-norbornene-2,3-dicarboximide ester (HONB, cat. 02321) were obtained from Chem Impex International. Sephadex G-50 fine (cat. 27,113-6) and G-50 medium (cat. 27,114-4), Sephadex G-100 fine (cat. 27,118-7) and G-100 medium (cat. 27,119-5) were obtained from Aldrich. Bio Gel P-100 fine (cat. 150-4174) and Gel P-100 medium (cat. 150-4170) were obtained from Bio-Rad. Boc-K(Boc)-L-His $H_2O$ for use in the Examples was synthesized as follows. A mixture of Boc-K(Boc)-Osu (31.85 g, 71.8 mmol), L-His (13.38 g, 86.2 mmol) and $NaHCO_3$ in a mixture of THF (100 ml) and $H_2O$ (100 ml) was stirred overnight at room temperature. The clear solution was condensed to remove THF. The aqueous residue was washed with diethyl ether (2×100 ml) then acidified to pH 3 with solid citric acid. After cooling the mixture overnight at 4° C., precipitates were filtered and washed with ice-cold water (25 ml). Products were dissolved in warm water (100 ml) and filtered while warm to remove a trace of insoluble materials. The clear solution was set aside overnight at 4° C. Crystalline products were filtered, washed with ice-cold water (20 ml), and dried over KOH pellets in vacuo, yield 22.9 g. Rf=0.71 (positive Paulys reaction, negative ninhydrin reaction, CH3/MeOH/conc. NH4OH=12/9/4). Elemental analysis for the theoretical formula C22H37N5O7H2O (Mw. 501.58). Calcd. C 52.68, H 7.84, N 13.96; Found. C 52.69, H 7.86, N 14.94.

Acetyl-O-succinimide ester for use in the Examples was synthesized as follows. An ice-cold mixture (−5–0° C.) of acetic acid (12.0 g, 0.20 mol. Aldrich, cat. 33,882-6, 99.99% pure) and N-hydroxysuccinimide (27.0 g, 0.24 mol) in THF (150 ml) was treated with dicyclohexyldicarbodiimide (43.3 g, 0.21 mol) in ice-cold THF (150 ml) under vigorous stirring. After the reaction mixture was stirred overnight at 4° C., precipitates were filtered off and the solution was condensed to dryness. Crystalline powders were suspended in ethyl acetate (350 ml) and insoluble materials were filtered off. Crystalline products appeared on condensing the solution to about 50 ml. Petroleum ether (200 ml) was added and the mixture was set aside overnight at 4° C. Crystalline precipitates were filtered, washed with petroleum ether (50 ml), and dried in vacuo, yield 29.0 g. Elemental analysis for the theoretical formula C6H7NO4 (Mw. 157.1). Calcd. C 45.86, H 4.49, N 8.91; Found. C 45.87, H 4.52, N 4.89.

Proteins used as molecular weight markers in the Examples were as follows (obtained from Sigma): alcohol dehydrogenase (cat. 8656, lot. 88H9285, Mw 150,000), beta-amylase (cat. A-8781, lot. 108H9276, sweet potato, Mw 200,000 for the $V_0$ determination), bovine serum albumin ["BSA"] (Cat. A-8531, lot. 115H9417, Mw 66,000), carbonic anhydrase (cat. C-7025, lot. 46H9401, bovine erythrocytes, Mw 29,000), cytochrome c (cat. C-7150, lot. 117H9283, horse heat Mw 12,400).

EXAMPLE 1.

Synthesis of Di·$nH_2O$ (i: generation, n: number of bound water molecules per dendrimer).

The Boc-protected dendrimer of ith generation, $BD_i$, was prepared by a divergent method using N,N'-bis(tert-butoxycarbonyl)-L-lysine succinimide active ester, Boc-K (Boc)OSu, as a branching agent and 1,4-diaminobutane, DAB, as an initiator core.

$BD_3$: $(DAB)K_2K_4[Boc-K(Boc)]_8$ was prepared as follows.

The general procedure for the preparation of $BD_{1-3}$ involves the iterative coupling of the active ester then deprotection of the Boo-groups with trifluoroacetic acid (TFA). The deprotection was carried at room temperature in TFA (100 mL for 10 g-dendrimer) for one hour. The resulting solution was condensed under reduced pressure. The oily residue was solidified with diethyl ether, and then dried over KOH pellets in vacuo (quantitative yield). The resulting salts (10 g were dissolved in water (100 mL) and adjusted to pH 9–10 with, 10N NaOH, followed by addition of 1.5- and (THF, 100 mL) and $NaHCO_3$, respectively, based on the number of available free amino groups on the dendrimer. The reaction mixture was stirred for one day at room temperature. At his point the reaction mixture was a clear solution. This solution was condensed to one half its volume and the resulting turbid aqueous mixture was agitated overnight at 4° C. The solids precipitated from this mixture were filtered and washed on the filter with 5% aqueous $NaHCO_3$, 5% aqueous citric acid, and water and then dried over KOH pellets in vacuo.

The dried solid (10 g) of $BD_1$ and $BD_2$ were purified by dissolving in ethyl acetate (100 mL) and precipitated by addition of petroleum ether (300 mL). The dried solid of $BD_3$ (10 g) was dissolved in 2-propanol and precipitated by addition of petroleum ether (150 mL). The resulting gelatinous mixture was transferred to a centrifuge tube and spun at 5,000 rpm. The supernatant was removed and the pellet was washed with petroleum ether, and dried in vacuo. The yield ranged from 88–95% for several different trials.

Elemental analysis for $BD_3$: $(DAB)K_2K_4[Boc-K(Boc)]_8$, theoretical formula $C_{168}H_{308}N_{30}O_{48}$ (Mw. 3516). Calcd. C 57.38, H 8.83, N 11.95%; Found. C 57.33, H 8.79, N 11.98%.

EXAMPLE 2.

$BD_5$, $(DAB)K_2K_4K_8H_{16}[Boc-K(Boc)]_{16}$, was prepared from $BD_3$ as follows.

$BD_3$ (7.736 g, 2.20 mmol) was dissolved in TFA (50 mL). With vigorous stirring dry HBr gas was bubbled into the solution for 30 min. at room temperature. The nitrogen gas was passed through the mixture to remove excess HBr. The product was precipitated as the HBr salt by addition of diethyl ether and dried in vacuo, quantitative yield. The salts and HONB (6.60 g, 37.0 mmol) were dissolved in 100 mL of dimethylformamide DMF) and the solution was adjusted to pH 9–10 with triethyl amine. To this solution was added Boc-K(Boc)-L-histidine·$H_2O$ (19.42 g, 38.7 mmol). The resulting solution was cooled to 4° C. in an ice bath, stirred vigorously and treated with 50 mL of ice-cold solution of dicyclohexylcarbodiimide (7.26 g, 37 mmol) in DMF. The mixture was stirred for 2 days at 4° C. Precipitates were filtered off and the clear solution was condensed to dryness under reduced pressure. The residue was suspended in aqueous 5% $NaHCO_3$ (500 mL) and the mixture was agitated overnight at 4° C. The precipitated solids were collected, washed with 5% aqueous $NaHCO_3$ and water then dried over KOH pellets in vacuo. The suspension of products in ethanol (200 mL) was refluxed for 30 min. and filtered while warm. The filtrated was condensed and semisolid residues were solidified with diethyl ether (200 mL). The solid materials were filtered and dried in vacuo, and then were dissolved in warm ethyl acetate (80 mL) and filtered to remove a trace of insoluble materials. On cooling the filtrate to the room temperature solid products precipitated. The complete precipitation of products was accomplished by addition of diethyl ether (800 mL) and storing overnight at 4° C. After filtration and drying in vacuo the yield was 17.6 g (1.68 mmol, 76.2%) of pure product as an ethanol adduct Elemental analysis for $BD_5$, $(DAB)K_2k_4K_8H_{16}[Boc-K(Boc)]_{16}$: theoretical formula $C_{440}H_{770}N_{110}O_{112} \cdot 24C_2H_5OH$ (Mw. 10,499.2). Calcd. C 55.83, H 8.78, N 14.68, O 20.72%; Found. C 55.84, H 8.86, N 14.680%.

EXAMPLE 3.

$BD_{6-8}$ were prepared as follows.

The coupling of Boc-K(Boc)OSu with $D_{5-8}$·HBr followed the same procedure as for $D_{1-3}$, but for complete coupling the reaction required 3 days at least. The crude solid products of $BD_{6-8}$ were obtained by condensing the reaction mixture to one half its volume under reduced pressure and agitating the aqueous mixture at pH 8–9 for several hours at 4° C. The products were filtered, washed with 5% aqueous $NaHCO_3$ and water and then dried over KOH pellets in vacuo. The purification was performed by dissolution of the product in THF (50 mL for 10 g of product) and precipitation with petroleum ether (800 mL). The resulting gelatinous mixture was centrifuged at 5,000 rpm. The supernatant was removed, and the pellet was washed with petroleum ether and then dried over KOH pellets in vacuo. The yield was 88–91%.

Elemental analyses.

$BD_6$, $(DAB)K_2K_4K_8H_{16}K_{16}[Boc-K(Boc)]_{32}$: theoretical formula $C_{792}H_{1380}N_{174}O_{208}$ (Mw. 16,668.6). Calcd. C 57.07, H 8.34, N 14.62, O 19.97%; Found. C 57.10, H 8.38, N 14.60%.

$BD_7$, $(DAB)K_2K_4K_8H_{16}K_{16}K_{32}[Boc-K(Boc)]_{64}$: theoretical formula $C_{1496}H_{2660}N_{302}O_{400}$ (Mw. 31,279.1). Calcd. C 57.44, H 8.57, N 13.52, O 20.46%; Found. C 57.38, H 8.60, N 13.48%.

$BD_8$, $(DAB)K_2K_4K_8H_{16}K_{16}K_{32}K_{64}[Boc-K(Boc)]_{128}$: theoretical formula $C_{2904}H_{5520}N_{558}O_{784}$ (Mw. 60,500.1). Calcd. C 57.65, H 9.20, N 12.92, O 20.73%; Found. C 57.68, H 9.17, N 12.91%.

EXAMPLE 4.

$D_{6-8}$·HBr salts were purified before proceeding to the next process, while $D_5$·HBr was used without purification.

Figure 2A:
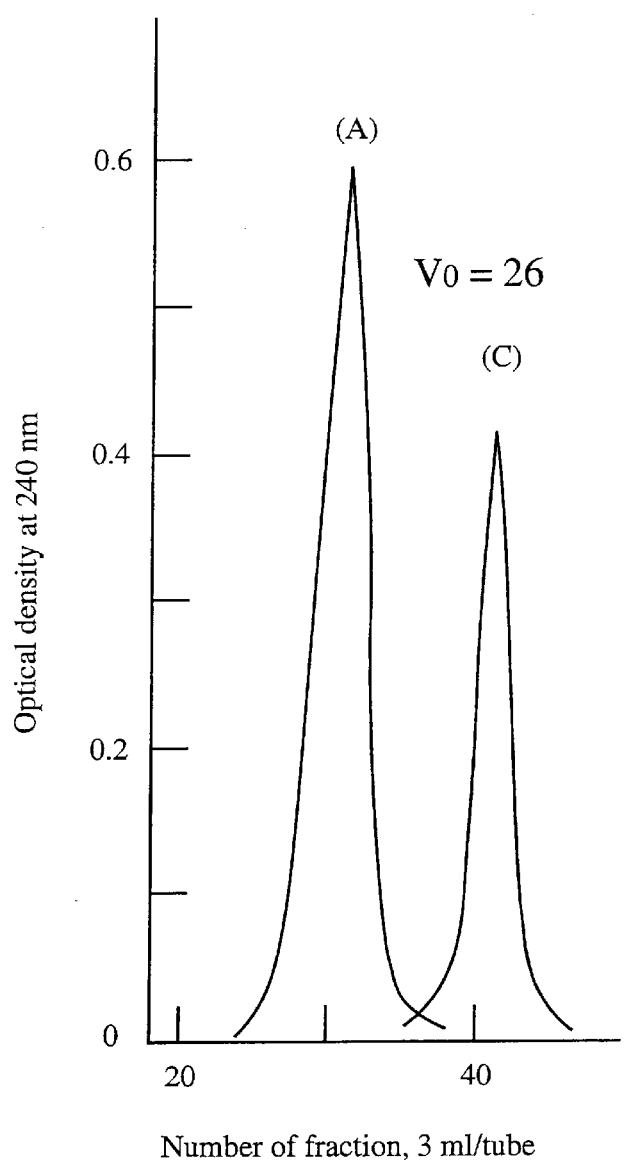
FIGS. 2A, 2B are plots showing separation of purified dendrimer constructs $D_i \cdot nH_2O$ (where $i$, the generation number, is 6, 7, and 8) according to the invention, as described below, by gel filtration at 23–25° C. The solvent system was 0.10 M ammonium formate with 5 volume % glycerol; linear flow rate was 4.3; column size was 2×90 cm. (A) is the peak for $D_7 \cdot nH_2O$ (100 mg/3 ml) on Sephadex G-50 fine; (B) is the peak for $D_8 \cdot nH_2O$ (100 mg/3 ml) on Bio Gel P-100 fine; (C) is the peak for $D_6 \cdot nH_2O$ (90 mg/3 ml) on Sephadex G-50 fine.
Figure 2B:
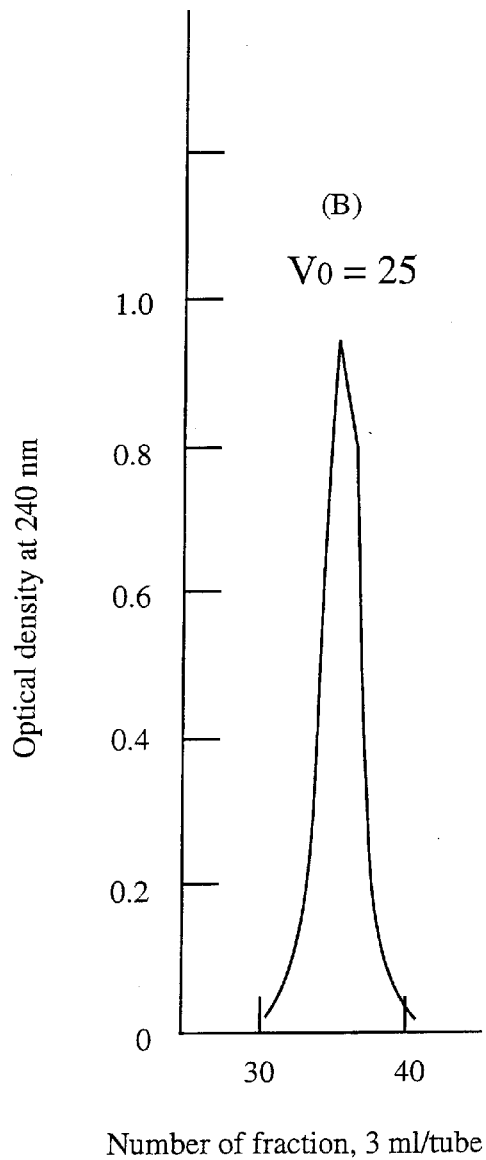

Crude HBr salts of $D_{6-8}$ were purified by size exclusion chromatography on a 5×50 cm column. For $D_6$~HBr and $D_7$~HBr the column was packed with a matrix of Sephadex G-50 medium. For $D_8$~HBr the column matrix was Sephadex G-100 medium. The matrix was equilibrated with 0. 10 M ammonium formate and the products were eluted with the same solvent. The fractions containing high molecular weight materials were combined and dialyzed extensively against double distilled water in tubing with molecular weight cut off ($Mw_{co}$) of 8,000. The dialyzed solution was lyophilized then further dried over $P_2O_5$ in vacuo (0.1–0.15 mm Hg), yield ~83% based on crude products. A portion of the purified products was re-chromatographed on a size exclusion chromatography column (2×90 cm) packed with Sephadex G-50 fine for $D_{6\&7} \cdot nH_2O$ and Bio Gel P-100 fine for $D_8 \cdot nH_2O$ to check the purity of products and estimate their molecular weight ($Mw^{GF}$). The equilibrium and elution media was 0.1 M ammonium formate containing 5 volume % of glycerol. The elution profiles of all three dendrimers were shown in FIG. 2. The $Mw^{GF}$ was estimated on the calibration curve of log Mw of proteins vs. $V_e/V_o$, where $V_e$ and $V_o$ are the elution volume of product and the column void volume, respectively. Proteins used as markers were beta-amylase (sweet potato, Mw 200,000 for the $V_o$ determination), albumin (bovine serum; Mw 66,000), carbonic anhydrase (bovine erythrocytes, Mw 29,000), cytochrome c (horse heart Mw 12,4000) and aprotinin (bovine lung, Mw 6,500).

The results are shown in Table I. The elemental analysis revealed that a ratio of number of carbon atoms to nitrogen atoms (C/N), which should be independent of variable degree of hydration, was in excellent agreement with theory for non-hydrated molecular formula with $Mwi^o$ of each dendrimer (see Table I). Thus, the estimated molecular weight ($Mw^{E.A}$) of hydrated dendrimer based on elemental analysis equals ($Mwi^o+18.01\times n$), in which n can be estimated using experimental values of carbon or nitrogen content. The numbers of free amino groups per dendrimer, determined calorimetrically according to the Habeeb method, was in good agreement with theory as shown in Table I.

elution medium. The Molecular weight (Mw) was estimated as for precursors.

The elution profile of $D_7(Ac^m)\cdot nH_2O$ revealed two peak fractions with $Mw^{G.F}$54,600 and 25,300. The same elution profile was observed when the fraction of $Mw^{G.F}$54,600 was re-fractionated. The elemental analysis of both fractions gave the same $Mw^{E.A}$ of 26,900 with m=115 and n=199, which was close to $Mw^{G.F}$25,300. As the $Mw^{G.F}$54,600 was about twofold that of $Mw^{E.A}$, it was concluded that $D_7(Ac^{115})\cdot 199H_2O$ was in equilibrium between monomeric and dimeric dendrimers due to hydrophobic interaction.

TABLE I

Analysis of $D_i \cdot nH_2O$

| | $D_6 \cdot nH_2O$ | $D_7 \cdot nH_2O$ | $D_8 \cdot nH_2O$ |
|---|---|---|---|
| Elemental analysis[1] | C47.65, H8.82, N20.44 | C47.22, H9.30, N19.43 | C47.32, H9.43, N18.96 |
| Molecular formula[2] | $C_{472}H_{868}N_{174}O_{78}$ | $C_{856}H_{1636}N_{302}O_{144}$ | $C_{1624}H_{3172}N_{558}O_{272}$ |
| Molecular formula[3] | $C_{472}H_{868}N_{174}O_{78} \cdot 91\ H_2O$ | $C_{856}H_{1636}N_{302}O_{144} \cdot 184\ H_2O$ | $C_{1624}H_{3172}N_{558}O_{272} \cdot 354\ H_2O$ |
| C/N[4] | 2.719(2.713) | 2.834(2.833) | 2.910(2.910) |
| $Mw^{E.A}$ [5] | 11,900 | 21,800 | 41,200 |
| $Mw^{G.F}$ [6] | 11,300 | 23,800 | 42,200 |
| n[7] | 91 | 184 | 354 |
| $NH_2$/dendrimer[8] | 63.8(64) | 122(128) | 259(256) |
| $H_2O$/dendrimer[9] | 1.17 | 1.30 | 1.30 |

Notes:
[1]Found.
[2]Theoretical formula without bound water
[3]Molecular formula based on elemental analysis; assumes the same molecular formulas for theoretical and nonhydrated ones (see text).
[4]Ratio of number of carbon atoms to nitrogen atoms by elemental analysis; value in parentheses is for theoretical molecular formula without bound water.
[5]Molecular weight determined based on elemental analysis.
[6]Molecular weight estimated by gel filtration.
[7]Number of water molecules bound per dendrimer of $Mw^{E.A.}$.
[8]Calorimetrically determined number of free amino acid groups per dendrimer of $Mw^{E.A.}$. Number in parentheses is for theoretical molecular formula.
[9]Number of water molecules bound per amino acid residue.

EXAMPLE 5.

Synthesis of $D_{7\&8}(Ac^m)\cdot nH_2O$ (Ac=acetyl group, m=number of acetyl groups per dendrimer).

0.25 mmol of purified $D_7\cdot nH_2O$ or $D_8\cdot nH_2O$ was dissolved in DMF (50 arm) and the solution was adjusted to pH 9–10 with triethyl amine. To this solution was added 1.0 molar equivalent of triethyl amine and acetyl-O-succinimide ester to the available free amino groups on the dendrimer. The mixture was stirred for 3 days at room temperature then condensed to remove DMF under reduced pressure. A suspension of the residual products in water (100 mL) was dialyzed against water (6×4L) in tubing with a $Mw_{co}$8,000 for 2 days at 4° C. Insoluble materials were removed by centrifugation (5,000 rpm; the solution of $D_8$ derivatives was still slightly turbid). The crude products were isolated as powders by lyophilization, giving a yield ~80% based on the precursor. It was noted that the complete acetylation of amino groups took place when 1.1 equivalent acetyl-O-succinimide ester was used and the products were water insoluble.

Figure 3A:
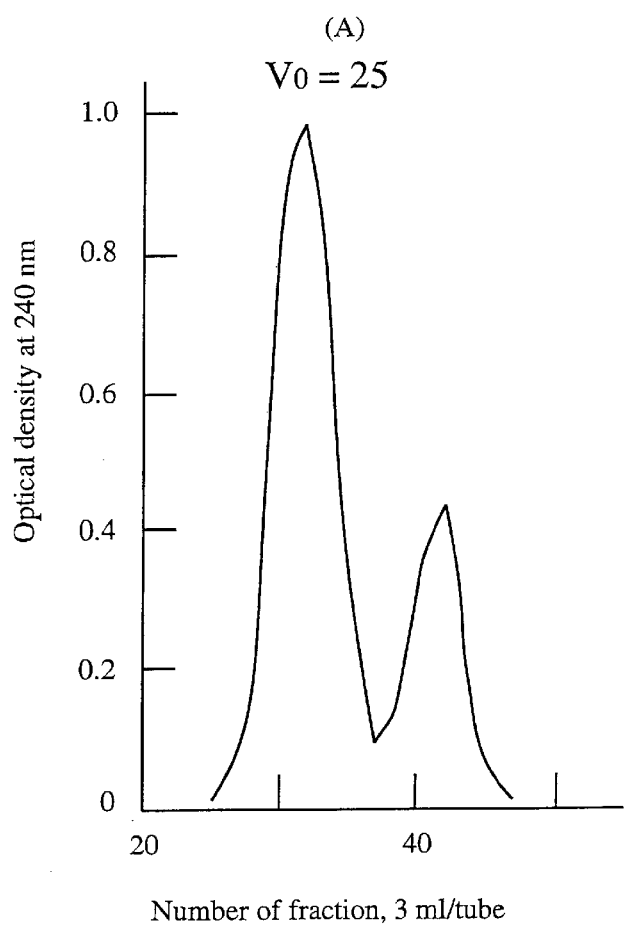
FIGS. 3A, 3B are plots showing separation of purified acetylated dendrimer constructs $D_i(Ac^m) \cdot nH_2O$ (where $i$ is 7 and 8) according to the invention, as described below, by gel filtration at 23–25° C. The solvent system was 0.10 M ammonium formate with 5 volume % glycerol; linear flow rate was 4.5; column size was 2×90 cm. (A) is the peak for $D_7(Ac^m) \cdot nH_2O$ (~100 mg/3 ml) on Bio Gel P-100 fine; (B) is the peak for $D_8(Ac^m) \cdot nH_2O$ (~50 mg/3 ml) on Sephadex G-100 fine.
Figure 3B:
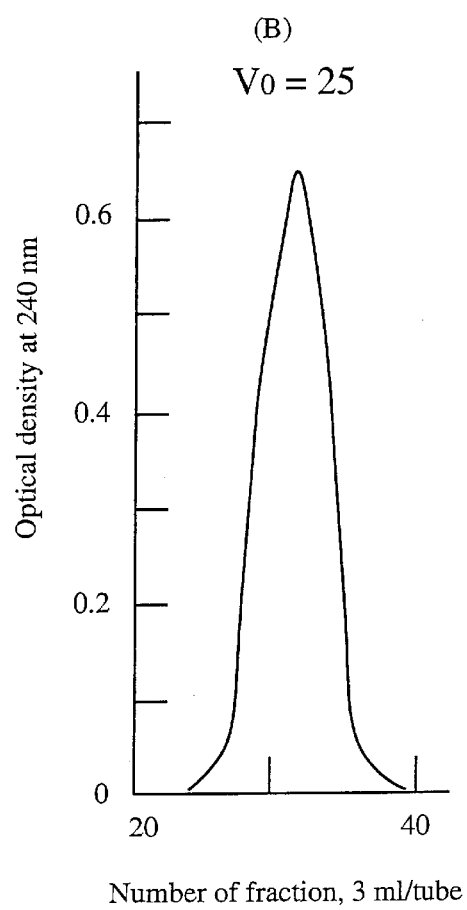

The crude products were purified by size exclusion chromatography (5×50 cm) packed with Bio Gel P-100 medium and Sephadex G-100 medium for $D_7$-and $D_8$-derivatives, respectively. 0.10 M ammonium formate was used as the equilibrium and elution medium. The major fractions were combined and dialyzed against double distilled water (6×4L) for 3 days at 4° C. in tubing with a $Mw_{co}$8,000. The products were taken up by lyophilization as powders. A portion of purified products was rechecked chromatographically on a 2×90 cm column (FIG. 3). 0.10 M ammonium formate plus 5 volume-% glycerol was used as the equilibrium and elution medium. The Molecular weight (Mw) was estimated as for precursors.

The elution profile of $D_8(Ac^m)\cdot nH_2O$, on the other hand, revealed only one peak fraction with $Mw^{G.F}$107,900, which was nearly twofold that of $Mw^{E.A}$51,200 with m=226 and n=210 (see Table II). Thus, $D_8(Ac^{226})\cdot 210H_2O$ was in the dimeric state.

EXAMPLE 6

Synthesis of $D_7(Ac^{115},PEG^m)\cdot nH_2O$ and $D_8(Ac^{226},PEG^m)\cdot nH_2O$ (PEG=poly(ethylene glycol) methyl ether, $Mw_n$ ca. 2,000 (Aldrich, Cat. 20,250-9, Lot. 9004-74-4). m=number of attached PEG molecules per dendrimer. n=number of water bound per dendrimer).

A suspension of acetylated dendrimer (0.14–0.05 mmol based on $Mw^{E.A}$) in DMF (100 mL) and a twofold molar excess of imidazole-activated PEG (C.O. Beauchamp et al., supra) based on available free amino groups was adjusted to pH 9–10 with triethyl amine. The mixture was stirred for 4 days at room temperature and then the mixture was condensed under reduced pressure. The residues were suspended in water (100 mL) and the mixture was dialyzed against double distilled water (6×4L) for 4 days at 4° C. in tubing with a $Mw_{co}$14,000. The turbid mixture was clarified by centrifugation (5,000 rpm), but $D_8$-derivatives were still slightly turbid. The solution was lyophilized, giving 90–93% based on its precursor. The products were subjected to size exclusion chromatographic purification on a 5×50 cm column packed with Bio Gel P-100 medium and Sephadex G-100 medium for $D_7$- and $D_8$-derivatives, respectively. 0.10 M ammonium formate was used for the equilibrium and the elution medium.

Figure 4A:
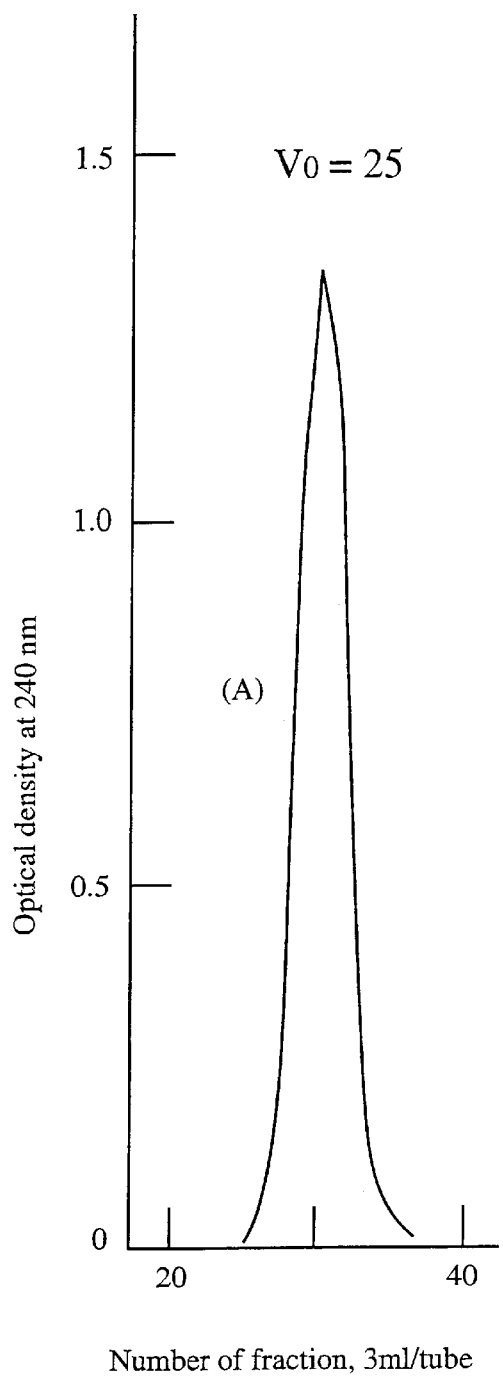
FIGS. 4A, 4B are plots showing separation of purified acetylated gycolated dendrimer constructs $D_i(Ac^m, PEG^m) \cdot nH_2O$ (where $i$ is 7 and 8) according to the invention, as described below, by gel filtration at 23–25° C. The solvent system was 0.10 M ammonium formate with 5 volume % glycerol; linear flow rate was 4.3; column size was 2×90 cm. (A) is the peak for $D_7(Ac^{115}, PEG^m) \cdot nH_2O$ (30 mg/3 ml) on Bio Gel P-100 fine; (B) is the peak for $D_8(Ac^{226}, PEG^m) \cdot nH_2O$ (20 mg/3 ml) on Sephadex G-100 fine.
Figure 4B:
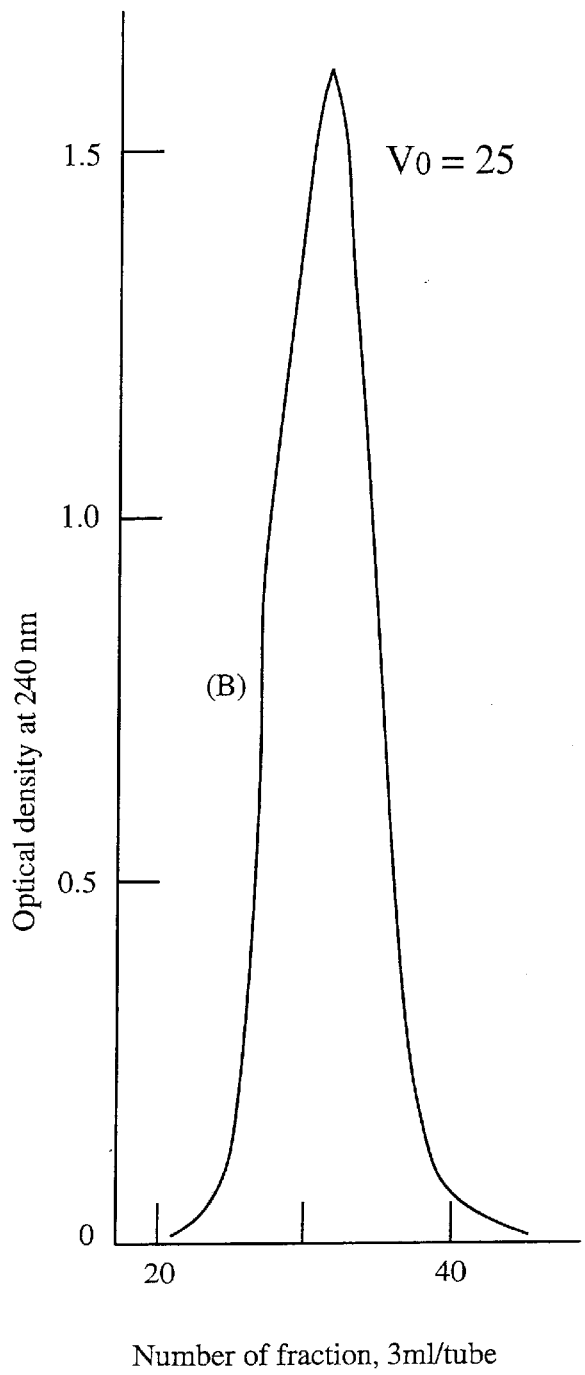

The elution profiles of both products revealed only one major peak fraction, in addition to a late running minor fraction of free activated PEG. The major fraction was dialyzed against water (6×4L) at 4° C. for 4 days in tubing with a $Mw_{co}$ 14,000, lyophilized then dried over $P_2O_5$ in vacuo (0.1–0.15 mm Hg) to give 79–82% yield based on the precursor. The $Mw^{G.F}$ of the products was estimated in the same manner as for their precursors on a 2×90 cm column (FIG. 4).

The $Mw^{G.F}$ of 58,200 was obtained for $D_7$-derivatives from the relatively sharp elution profile on Bio Gel P-100 fine. This molecular weight was close to $Mw^{E.A}$ 52,500 with molecular formula of $D_7(Ac^{115}, PEG^{13}) \cdot 210H_2O$ (see Table EIII). Therefore, this derivative is concluded to be monomeric without aggregation.

The elution profile of $D_8$-derivatives was rather broad (FIG. 4), suggesting the presence of aggregates. However, estimated $Mw^{G.F}$ 113,500 was in good agreement with $Mw^{EA}$ 109,100 of monomeric $D_8(Ac226,PEG^{30}) \cdot 400H_2O$ (Table III). It was concluded therefore that attached PEG chains covered all hydrophobic surfaces of these dendrimers and hence the hydrophobic interaction among dendrimers was prohibited.

TABLE II

Analysis of $D^i(Ac^m) \cdot nH_2O$

| | $D_7(AC^m) \cdot nH_2O$ | $D_8(AC^m) \cdot nH_2O$ |
|---|---|---|
| Elemental analysis[1] | C48.52, H8.51, N15.73 | C48.59, H8.68, N15.23 |
| Molecular formula | $C_{1086}H_{1866}N_{302}O_{259} \cdot 199H_2O$ | $C_{2069}H_{3617}N_{558}O_{495} \cdot 384H_2O$ |
| C/N[2] | 3.597 (3.596) | 3.721 (3.708) |
| $Mw^{E.A}$ [3] | 26,900 | 51,200 |
| $Mw^{G.F}$ [4] | 54,600; 25,300 | 107,900 |
| n[5] | 199 | 384 |
| m[6] | 115 | 226 |
| $NH_2$/dendrimer[7] | 12.3 | 28.9 |
| $H_2O$/dendrimer[8] | 1.40 | 1.40 |

Notes:
[1]Found.
[2]Ratio of number of carbon atoms to nitrogen atoms by elemental analysis; value in parentheses is for theoretical formula with m but without n.
[3]Molecular weight determined based on elemental analysis.
[4]Molecular weight estimated by gel filtration.
[5]Number of water molecules bound per dendrimer of $Mw^{E.A}$.
[6]Number of acetyl groups per dendrimer of $Mw^{E.A}$.
[7]Calorimetrically determined number of free amino acid groups per dendrimer of $Mw^{E.A}$.
[8]Number of water molecules bound per amino acid residue.

TABLE III

Analysis of $D^i(Ac^m,PEG^{m'}) \cdot nH_2O$

| | $D_7(AC^{115},PEG^{m'}) \cdot nH_2O$ | $D_8(AC^{226},PEG^{m'}) \cdot nH_2O$ |
|---|---|---|
| Elemental analysis[1] | C51.33, H8.86, N8.10 | C51.84, H9.08, N7.18 |
| Molecular formula | $C_{2243}H_{4180}N_{302}O_{831} \cdot 210H_2O$ | $C_{4698}H_{8876}N_{558}O_{1795} \cdot 400H_2O$ |
| C/N[2] | 7.390 (7.427) | 8.420 (8.420) |
| $Mw^{E.A}$ [3] | 52,500 | 109,000 |
| $Mw^{G.F}$ [4] | 58,200 | 114,000 |
| m'[5] | 12.9 | 29.5 |
| n[6] | 210 | 400 |
| $NH_2$/dendrimer[7] | 0 | 0 |
| $H_2O$/residue[8] | 1.48 | 1.48 |

Notes:
[1]Found.
[2]Ratio of number of carbon atoms to nitrogen atoms by elemental analysis; value in parentheses is for theoretical formula with m and m' but without n.
[3]Molecular weight determined based on elemental analysis.
[4]Molecular weight estimated by gel filtration.
[5]Number of poly(ethylene glycol) methyl ether (Mw. 1970, degree of polymerization = 44) bound per dendrimer of $Mw^{E.A}$.
[6]Number of water molecules bound per dendrimer of $Mw^{E.A}$.
[7]Calorimetrically determined number of free amino acid groups per dendrimer of $Mw^{E.A}$.
[8]Number of water molecules bound per amino acid residue.

EXAMPLE 7

Preparation of Copper Complexes of $D_{7\&8}(Ac^{m'}) \cdot nH_2O$ and $D_{7\&8}(Ac^{m'},PEG^{m'}) \cdot nH_2O$.

Figure 5:
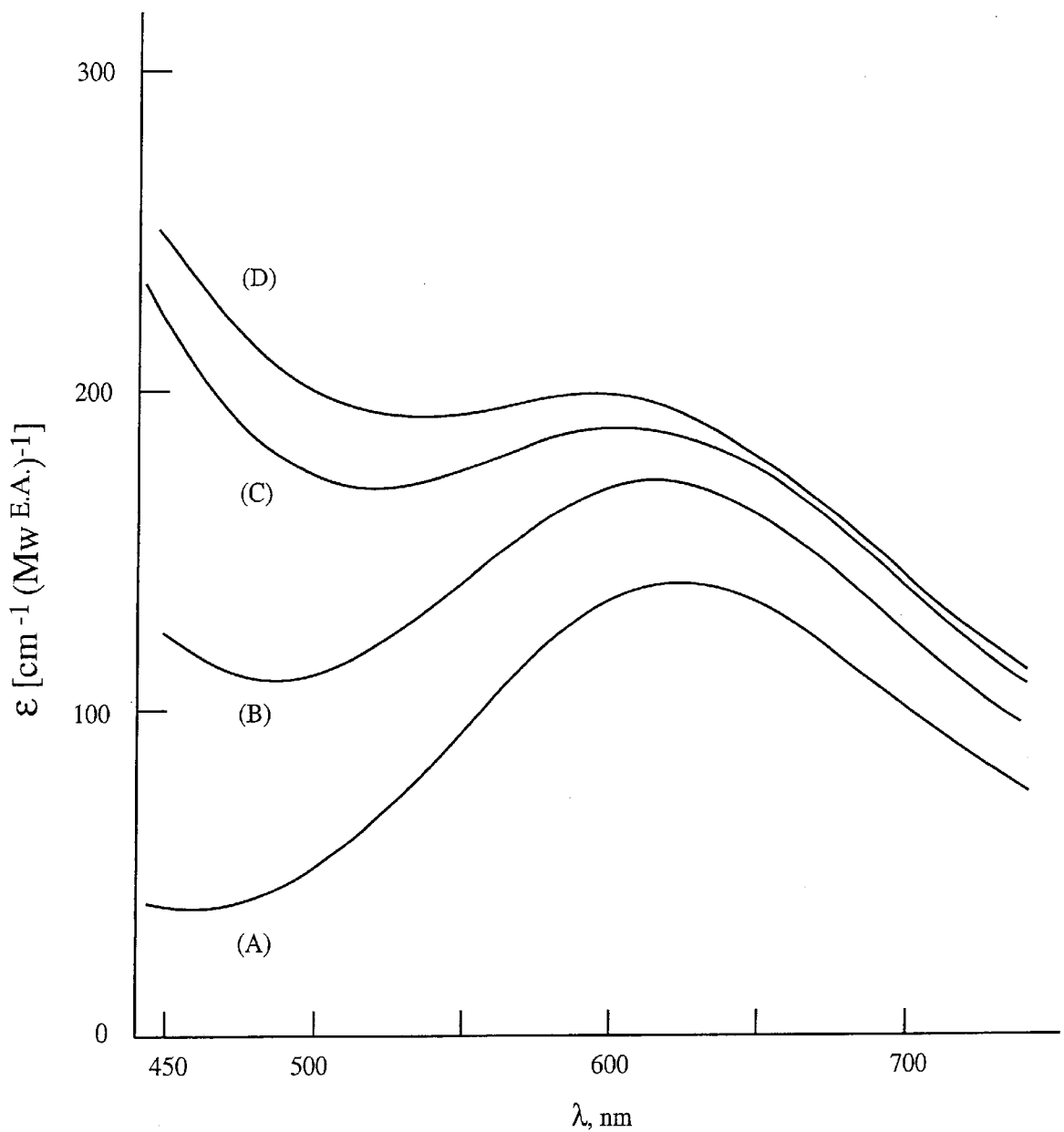
FIG. 5 is a plot of absorption spectra of $CuCl_2$-dendrimer complexes according to the invention in potassium phosphate at pH 7.80 and 25° C. (A) is $D_7(Ac^{115}, CuCl_2) \cdot 199H_2O$; (B) is $D_7(Ac^{115}, PEG^{13}, CuCl_2) \cdot 210H_2O$; (C) is $D_8(Ac^{226}, CuCl_2) \cdot 384H_2O$; (D) is $D_8(Ac^{226}, PEG^{30}, CuCl_2) \cdot 400H_2O$

Water used for preparation of copper complexes was firstly doubly distilled and then passed through a 10×50 cm column packed with chelex resins. The pH of water was 6.0–6.2.2.0 g of product was dissolved in water (50 mL) containing 30-times molar excess of $CuCl_2$ to dendrimer and the solution was stirred for 2 hours at room temperature. The resulting purple-colored solution was extensively dialyzed against water (one week) at 4° C. in tubing with a $Mw_{co}$14,000. The solution was filtered through a fine-sintered glass funnel. The filtrate was lyophilized and the purple-colored mica-like products were further dried over $P_2O_5$ in vacuo (0.1–0.15 mm Hg) for 2–3 days, giving 1.7–1.8 g of products. Elemental analysis (Table IV) revealed that for all copper complexes the ratio of numbers of elements, C:H:N, was nearly identical to that of the respective host dendrimers (compare the ratios in Table II and Table III). The number of $CuCl_2$ bound per dendrimer was 1.0–1.20 (average 1.05) by atomic absorption spectroscopy. The electronic absorption spectra shown in FIG. 5 (see also Table IV) exhibited maxima around 600–620 nm due to a d-d transition typical for a $CuN_4$ coordination, where four nitrogen atoms would belong to imidazole moieties.

TABLE IVA

Analysis of $CuCl_2$-Complex $D_7(Ac^{115})$ and $D_7(Ac^{115}, PEG^{13})$

| | $D_7(Ac^{115}, CuCl_2^m) \cdot nH_2O$ | $D_7(Ac^{115}, PEG^{13}, CuCl_2^m) \cdot nH_2O$ |
|---|---|---|
| Molecular formula[1] | $C_{1086}H_{1866}N_{302}O_{259} \cdot CuCl_2 \cdot 199 H_2O$ | $C_{2243}H_{4180}N_{302}O_{831} \cdot CuCl \cdot 210 H_2O$ |
| $Mw^{E.A}$ [2] | 27,018 | 52,597 |
| Elemental analysis[3] | C48.30, H8.41, N15.63, Cl 0.25 | C51.18, H8.79, N8.01, Cl 0.13 |
| Elemental analysis[4] | C48.28, H8.45, N15.66, Cl 0.26 | C51.22, H8.81, N8.04, Cl 0.14 |

TABLE IVA-continued

Analysis of $CuCl_2$-Complex $D_7(Ac^{115})$ and $D_7(Ac^{115}, PEG^{13})$

|  | $D_7(Ac^{115}, CuCl_2^m) \cdot nH_2O$ | $D_7(Ac^{115}, PEG^{13}, CuCl_2^m) \cdot nH_2O$ |
|---|---|---|
| $Cu^5$ | 2.48 mg/g | 1.27 mg/g |
| $m^6$ | 1.05 | 1.05 |
| $n^7$ | 199 | 210 |
| $\lambda_{max}^8$ | 625 nm | 612 nm |
| $\epsilon_{max}^9$ | 140 cm$^{-1}$ · M$^{-1}$ | 173 cm$^{-1}$ · M$^{-1}$ |

Notes:
[1] Molecular formula assumes the same formulas for nonhydrated host precursors (see Tables II and III) and nonhydrated host dendrimer of copper complex.
[2] $Mw^{E.A}$ estimated for m = 1.00.
[3] Found.
[4] Calculated.
[5] mg/gram of dendrimer, by atomic absorption.
[6] Average number of Cu(II) ion per dendrimer of $Mw^{E.A}$.
[7] Number of water molecules bound per dendrimer of $MW^{E.A}$.
[8] From absorption spectrum obtained in 50 mM potassium phosphate at pH 7.80, 25° C.
[9] From absorption spectrum obtained in 50 mM potassium phosphate at pH 7.80, 25° C.; molarity based on $Mw^{E.A}$.

TABLE IVB

Analysis of $CuCl_2$-Complex $D_7(Ac^{226})$ and $D_7(Ac^{226}, PEG^{30})$

|  | $D_8(Ac^{226}, CuCl_2^m) \cdot 384\ H_2O$ | $D_8(Ac^{226}, PEG^{30}, CuCl_2^m) \cdot nH_2O$ |
|---|---|---|
| Molecular formula[1] | $C_{2069}H_{3617}N_{558}O_{495} \cdot CuCl_2 \cdot 384\ H_2O$ | $C_{4698}H_{8876}N_{558}O_{1795} \cdot CuCl \cdot 400\ H_2O$ |
| $Mw^{E.A}$ [2] | 51,284 | 109,248 |
| Elemental analysis[3] | C48.44, H8.66, N15.21, Cl 0.13 | C51.45, H8.99, N7.12, Cl 0.06 |
| Elemental analysis[4] | C48.46, H8.62, N15.24, Cl 0.14 | C51.65, H8.93, N7.15, Cl 0.065 |
| $Cu^5$ | 1.30 mg/g | 0.61 mg/g |
| $m^6$ | 1.05 | 1.05 |
| $n^7$ | 384 | 400 |
| $\lambda_{max}^8$ | 602 nm | 600 nm |
| $\epsilon_{max}^9$ | 187 cm$^{-1}$ · M$^{-1}$ | 197 cm$^{-1}$ · M$^{-1}$ |

Notes:
[1] Molecular formula assumes the same formulas for nonhydrated host precursors (see Tables II and III) and nonhydrated host dendrimer of copper complex.
[2] $Mw^{E.A}$ estimated for m = 1.00.
[3] Found.
[4] Calculated.
[5] mg/gram of dendrimer, by atomic absorption.
[6] Average number of Cu(II) ion per dendrimer of $Mw^{E.A}$.
[7] Number of water molecules bound per dendrimer of $Mw^{E.A}$.
[8] From absorption spectrum obtained in 50 mM potassium phosphate at pH 7.80, 25° C.
[9] From absorption spectrum obtained in 50 mM potassium phosphate at pH 7.80, 25° C.; molarity based on $Mw^{E.A}$.

EXAMPLE 8.

In Vitro Catalytic Activity for Superoxide Dismutation.

The catalytic activity of dendritic copper complexes for the dismutation reaction, $2O_2^- + 2H^+ \rightarrow H_2O_2 + O_2$, was followed by the fraction of inhibition ($f_i$) for the cytochrome c reduction by superoxide radicals generated in the xanthine-xanthine oxidase system at 25° C. using an assay method described generally in J. M. McCord et al. 1969, *Jour. Biol. Chem.*, Vol. 244(22), pp. 6049 ff., as follows. The solvent system was 50 mM potassium phosphate buffer at pH 7.80 containing cytochrome c from horse heart (Sigma, cat. C-2506 lot. 18H7001) at a final concentration of final concentration of $10^{-5}$ M and xanthine (Calbiochem, cat. 6820, lot. 046290 at a final concentration of $5 \times 10^{-8}$ M. Superoxide was generated by adding xanthine oxidase from buttermilk (Sigma, cat. X-4376, lot. 88H3794) to the buffered solvent to an initial concentration of $10^{-8}$ M. The optical density vs. reaction time was followed on a Shimazu recording spectrophotometer, model UV-3100. The rate of increase in optical density at 550 nm of the resulting test solution (3 ml, optical path length 10 mm) in the absence of dendritic copper complexes or SOD ranged from 0.018–0.022 over a 0–90 sec. reaction interval. Reagents and other materials used in this and the following Examples were: CuZn-SOD from bovine erythrocytes (Boehringer Mannheim GmbH, cat. 837-113, lot. 11134421-16); $KH_2PO_4$ (cat. 22,980-6, 99.99% pure), $K_2HPO_4$ (cat. 45,020-0, 99.998% pure) and ethylenediaminetetraacetic acid ("EDTA") (cat. 43,178-8, 99.999% pure) from Aldrich; bovine serum albumin ("BSA") (Sigma, cat. A -8531, lot. 115H9417).

Figures 6A, 6B:
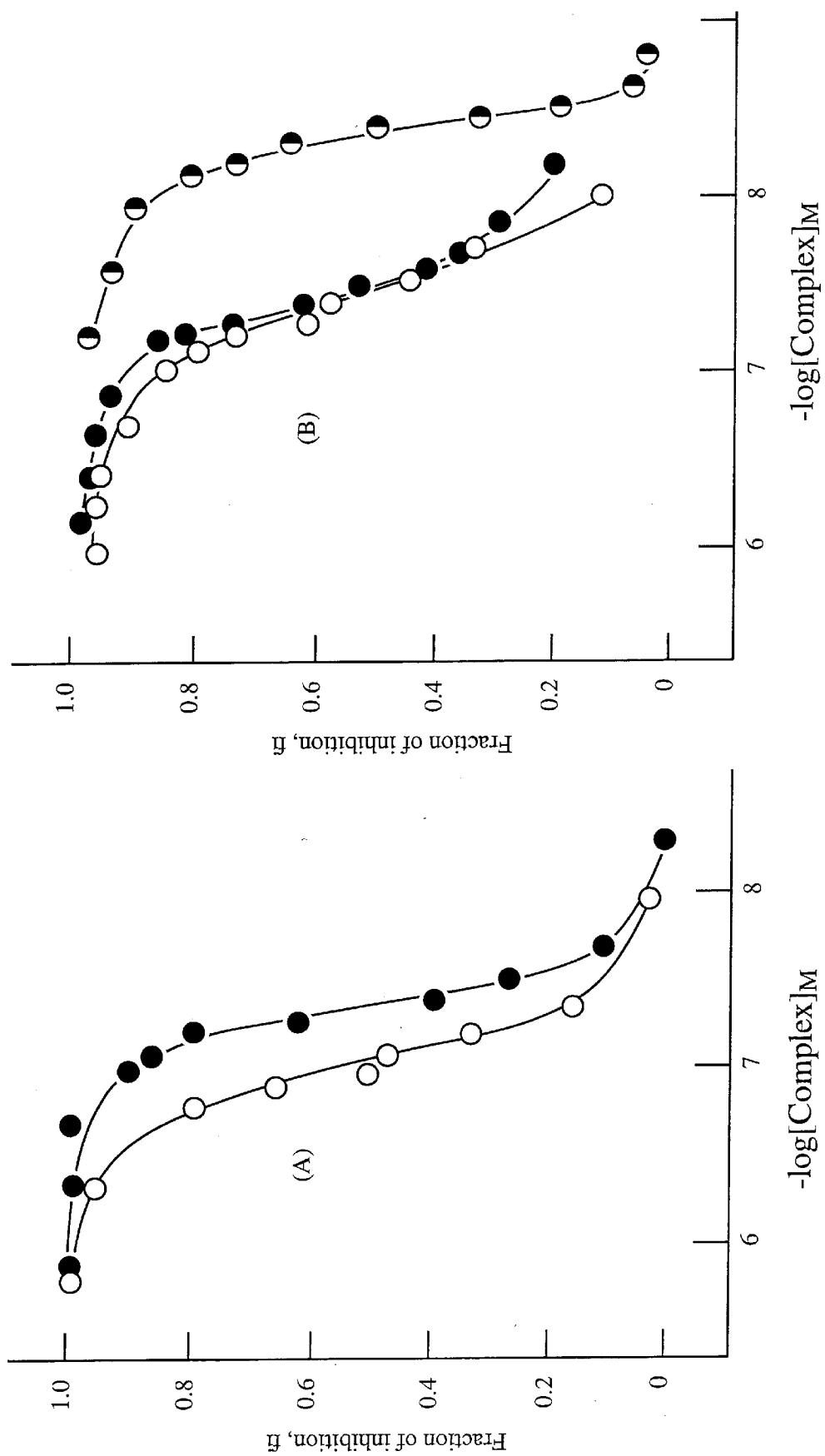
FIGS. 6A, 6B are plots showing inhibition of reduction of cytochrome c by superoxide in the presence of four $CuCl_2$-dendrimer complexes according to the invention, and in the presence of superoxide dismutase ["SOD"]. The solvent system was 50 mM potassium phosphate at pH 7.80, 25° C.; $10^{-5}$ M cytochrome c, $5\times10^{-5}$ M xanthin, $10^{-8}$ M xanthin oxidase. (A): open circles, $D_7(Ac^{115}, CuCl_2) \cdot 199H_2O$; filled circles, $D_7(Ac^{115}, PEG^{13}, CuCl_2) \cdot 210H_2O$; (B): open circles, $D_8(Ac^{226}, CuCl_2) \cdot 384H_2O$; filled circles, $D_8(Ac^{226}, PEG^{30}, CuCl_2) \cdot 400H_2O$; half-filled circles, SOD.

In the assay of hiss Example (results in Table V and FIG. 6) EDTA was omitted in order to examine its effect on the activity separately. By definition one unit ($IC_{50}$, half inhibitory concentration of copper complex) is equivalent to the amount of complex required to inhibit the cytochrome c reduction by 50%; that is, the $IC_{50}$ is lower for higher inhibitory activity. The profiles of $f_i$ vs. log molar concentration of copper complexes shown in FIG. 6 reveals that the maximum inhibition in the presence of high concentration of all copper complexes was more than 0.95, indicating a fast reaction rate of the complex with superoxide radical. Estimated $IC_{50}$ values were listed in Table V. As all complexes carried an equivalent number of copper active sites (average 1.05 per molecule), effects of generation-increase and of attached PEG chains on the activity can be examined straightforwardly.

The activity of $D_7(Ac^{115}, PEG^{13}, CuCl_2) \cdot 210H_2O$ ($Mw^{E.A}52,600$) was about 2.1 times higher than that of $D_7(Ac^{115}, CuCl_2) \cdot 199H_2O$ ($Mw^{E.A}26,900$), indicating that the increase of molecular weight of dendrimer and/or the PEG attachment enhanced the inhibitory activity. However, no such profound increase of activity was observed when compared the activity levels of two $D_8$-derivatives; glycolated $D_8$-derivatives ($Mw^{E.A}109,200$) had only 1.1 times higher activity than acetylated $D_8$-derivatives with $Mw^{E.A}51,300$ although the molecular weight of the former was two times that of the latter. Glycolated $D_7$ and acetylated $D_8$ had nearly the same molecular weights and similar activity levels. With PEG on the outermost tier, glycolated $D_7$ can be regarded as a 8th generation dendrimer, being a homolog of acetylated $D_8$, thus these two homologs would have the similar activity levels. Accordingly it appears that increasing the number of generations, including PEG chains as a tier, from 7th to 8th profoundly enhanced the activity. On further increasing the number of generations above 9th, the $IC_{50}$ value seemed to converge quickly to $3 \times 10^{-8}$ M. This lowest level is the same with that observed for the rigid complex of bis[cyclo(histidylhistidyl)]$Cu^{2+}$, in which a copper ion coordinates with four nitrogen atoms from imidazole groups forming a $CuN_4$ coordination sphere as an active center. (See, S. Kubota et al. 1984, *Proc. Natl. Acad Sci. USA*, Vol 81, pp 3283–86.)

The active site in bovine CuZn-SOD is the distorted square-planar $CuN_4$ coordination sphere, in which four N atoms belong to imidazole moiety of His-44, -46, -61 and -118 (See, J. S. Richardson et al. 1975, *Proc. Nat. Acad Sci. USA*, Vol. 72(4), pp. 1349 ff.). One side of the plane is projected to the tripeptide fragment of His44-Val45-His46, which blocks access of solvents to $Cu^{2+}$ ion from this site. Solvents are accessible from other site of plane by means of conical channel. Positively charged Lys-134 along the channel located near at the protein surface is thought to drive superoxide anion down into the channel toward the active site. The efficient catalytic activity of CuZn-SOD is attributed to such a beneficial morphology.

Dendrimers described in the Examples, having asymmetric branch junctures, are highly fractal and the interior zones of these will less ordered than in dendrimers having symmetric branch junctures. Some areas of the outermost tier are tethered closer to the active site than others. Thus, the distance from the active site to the dendrimer surface is variable and the surface is uneven. A dendrimer having globular shape with an even surface spaced a homogeneous distance from the center can be constructed for example by attaching spacers having the general formula, e.g., $NH_2(CH_2)_nCOOH$, such as β-alanine (n=2), 4-aminobutyric acid (n=3), 5-aminovaleric acid (n=4), to the α-amino group of at least some of the building blocks except the histidyl residues. The morphology of the dendrimer surface and inner cavities as well as the surface porosity, can influence the SOD activity level, the stability of the dendrimer molecule and the active site locus.

TABLE V

| | $IC_{50}$[1] |
|---|---|
| $D_7(Ac^{115},CuCl_2).199H_2O$ | $9.1 \times 10^{-8}$M |
| $D_7(Ac^{115},PEG^{13},CuCl_2).210H_2O$ | $4.4 \times 10^{-8}$M |
| $D_8(Ac^{226},CuCl_2).384H_2O$ | $3.6 \times 10^{-8}$M |
| $D_8(Ac^{226},PEG^{30},CuCl_2).400H_2O$ | $3.2 \times 10^{-8}$M |

Note:
[1]Half inhibitory concentration of $CuCl_2$-dendrimer complex for inhibition of superoxide reduction by cytochrome c.

EXAMPLE 9

Firstly we examined the effect of small molecular EDTA as a probe on the inhibitory activity of complexes. Copper ions associated with almost all amino acids and small peptides and majority of isolated proteins will be liberated from ligands by EDTA by forming copper complexes with a very high stability constant but with no activity for the superoxide dismutation, leading to destabilization of molecular structures and the deactivation of enzymes.

Figure 7A:
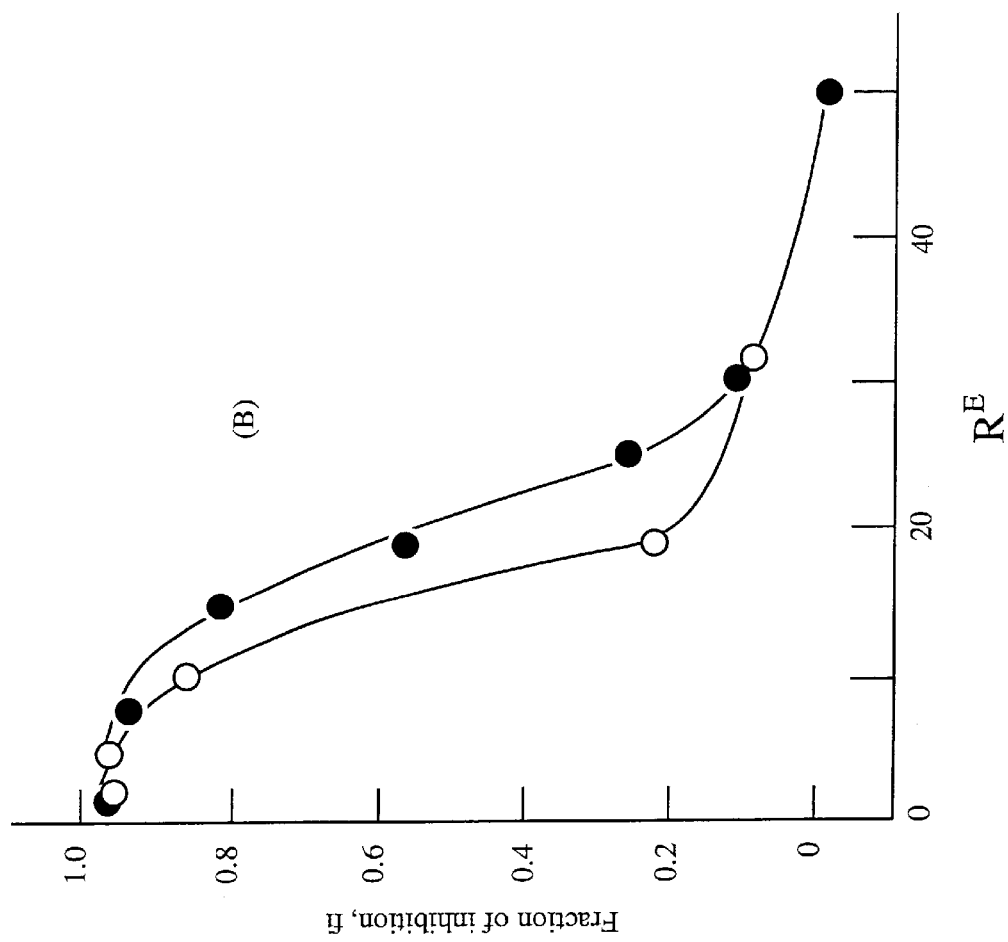
FIGS. 7A, 7B are plots showing effect of EDTA on inhibition of reduction of cytochrome c by superoxide in the presence of fixed concentrations of four $CuCl_2$-dendrimer complexes according to the invention. $R^E$ is a molar ratio of EDTA to $CuCl_2$-dendrimer complex. The solvent system was 50 mM potassium phosphate at pH 7.80, 25° C.; $10^{-5}$ M cytochrome c, $5\times10^{-5}$ M xanthin, $10^{-8}$ M xanthin oxidase. (A): open circles, $D_7(Ac^{115}, CuCl_2) \cdot 199H_2O$ ($2.48\times 10^{-6}$ M; filled circles, $D_7(Ac^{115}, PEG^{13}, CuCl_2) \cdot 210H_2O$ ($1.07\times10^{-6}$ M); (B): open circles, $D_8(Ac^{226}, CuCl_2) \cdot 384H_2O$ ($1.10\times10^{-6}$ M; filled circles, $D_8(Ac^{226}, PEG^{30}, CuCl_2) \cdot 400H_2O$ ($0.70\times10^{-6}$ M).
Figure 7B:
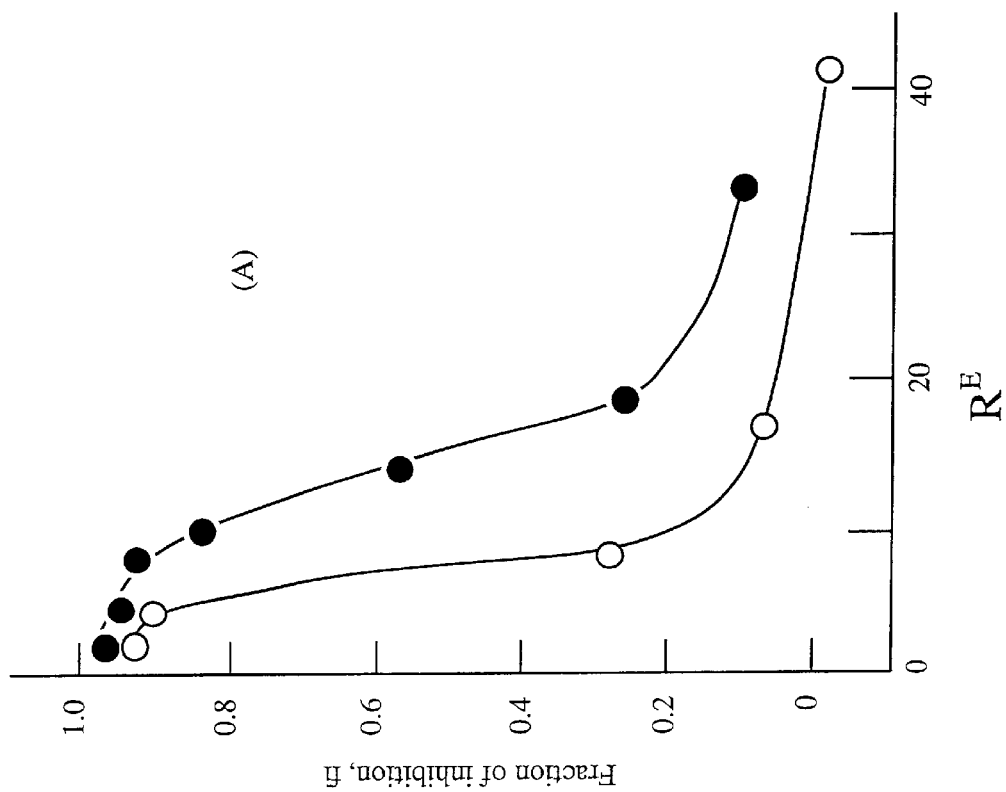

In FIG. 7 and Table VI are shown profiles of $f_i$ vs. the molar ratio of EDTA to dendrimers ($R^E$) and $R^E_{50}$ at $f_i=0.50$. FIG. 7(A) on $D_7$ dendrimers clearly indicated that the presence of PEG chains profoundly enhanced the protection for the active site from EDTA attack. Thus, glycolated $D_7$ with $R^E_{50}=15$ was two times more stable than acetylated $D_7$ with $R^E_{50}=6$ against EDTA.

This was also the case for D8 dendrimers, although the protective effect by PEG chains was not appreciably high. Glycolated $D_7$ could be regarded as an 8th generation homolog of acetylated 8th dendrimer as discussed above so that the similar $R^E_{50}$ for both dendrimers was expected (see Table VI). The stability constant of $CuN_4$ in our dendrimers would be less than that of EDTA-$Cu^{2+}$(1:1) complex with about logK=19. If the free access of EDTA to the active site is assumed, $R^E_{50}$ would be attained at $R^E=1$. Thus, a large excess molar EDTA required for the deactivation of complexes by 50% indicated the severe interference for EDTA to reach the copper active site.

Such interference could be due to the steric hindrance in tiers and/or smaller size of pores on the dendrimer surface. It was concluded therefore that a pile of more tiers over the active site locus could provide more effective protection for active sites against small molecular and strong chelating agents such as EDTA.

TABLE VI

| | Concentration[1] | $R^E_{50}$[2] |
|---|---|---|
| $D_7(Ac^{115},CuCl_2).199H_2O$ | $2.49 \times 10^{-6}$M | 6 |
| $D_7(Ac^{115},PEG^{13},CuCl_2).210H_2O$ | $1.06 \times 10^{-6}$M | 15 |
| $D_8(Ac^{226},CuCl_2).384H_2O$ | $1.10 \times 10^{-6}$M | 16 |
| $D_8(Ac^{226},PEG^{30},CuCl_2).400H_2O$ | $0.70 \times 10^{-6}$M | 20 |

Note:
[1]Concentration of $CuCl_2$-dendrimer complex in mixtures containing differing concentrations of EDTA.
[2]Molar ratio of EDTA to complex required for 50% inhibition of superoxide reduction by cytochrome c.

TABLE VII

Interference by BSA with CuCl$_2$-Dendrimer Complex Activity

| | $R^B_{50}$[1] | $f_{im}$[2] | $R^B_m$[3] | $f_i$[4] | $R^{B,}$[5] |
|---|---|---|---|---|---|
| D$_7$(Ac$^{115}$,CuCl$_2$).199H$_2$O | 6.7 | — | — | 0.32 | 63 |
| D$_7$(Ac$^{115}$,PEG$^{13}$,CuCl$_2$).210H$_2$O | 13 | 0.06 | 37 | 0.30 | 147 |
| D$_8$(Ac$^{226}$,CuCl$_2$).384H$_2$O | 13 | 0.12 | 35 | 0.26 | 143 |
| D$_8$(Ac$^{226}$,PEG$^{30}$,CuCl$_2$).400H$_2$O | 15 | 0.07 | 56 | 0.14 | 225 |

Notes:
[1]Molar ratio of BSA to CuCl$_2$-dendrimer complex required for 50% inhibition of superoxide reduction by cytochrome c.
[2]Minimum fraction of inhibition.
[3]Molar ratio of BSA to complex at minimum fraction of inhibition.
[4]Fraction of inhibition in the presence of 1 wt. % BSA.
[5]Molar fraction of BSA to CuCl$_2$-dendrimer complex.

EXAMPLE 10

This example illustrates how large molecular proteins would affect the inhibitory activity of the complexes.

Serum albumins are abundant in living organisms. Bovine serum albumin (BSA) has Mw 66,000 and its amino terminal fragment is capable of binding one Cu$^{2+}$ relatively strongly. The copper- BSA complex, however, has practically no SOD-like activity. Therefore, copper-free BSA was used as a probe and EDTA was omitted from test system (see caption for Table VII).

Figure 8B:
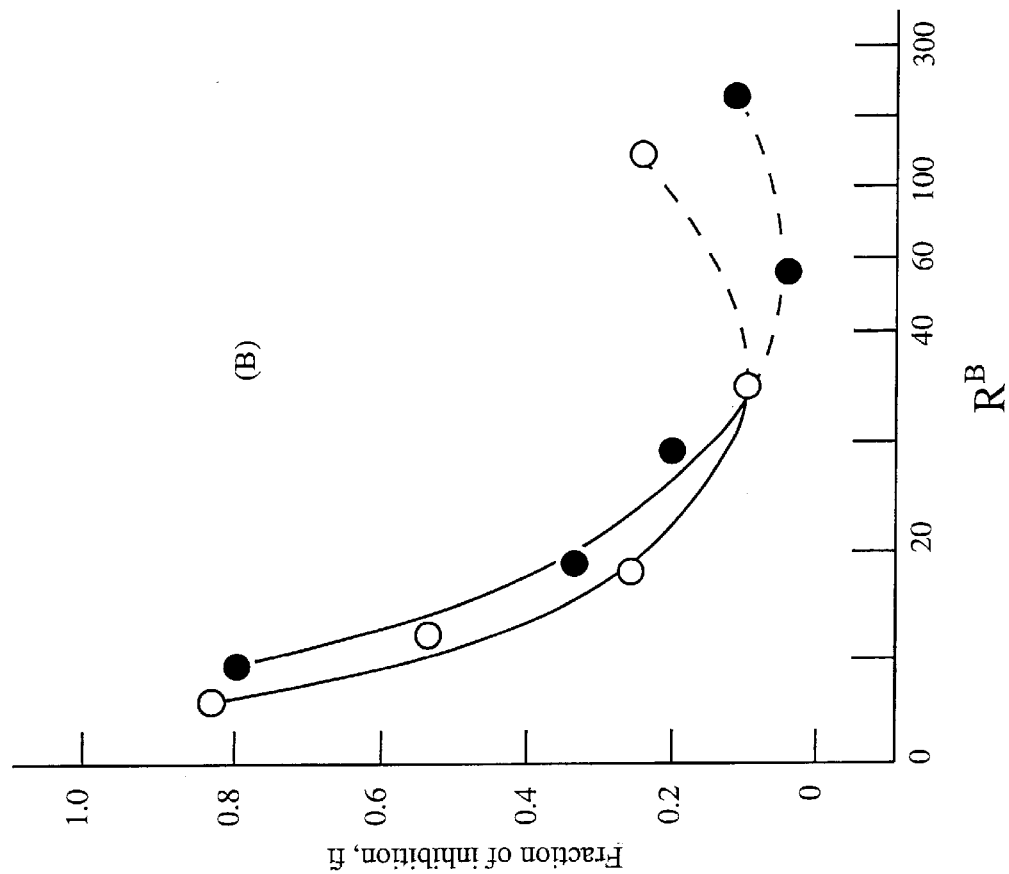
FIGS. 8A, 8B are plots showing effect of bovine serum albumin ["BSA"] on inhibition of reduction of cytochrome c by superoxide in the presence of fixed concentration of four $CuCl_2$-dendrimer complexes according to the invention. $R^B$ is a molar ratio of BSA to $CuCl_2$-dendrimer complex The solvent system was 50 mM potassium phosphate at pH 7.80, 25° C.; $10^{-5}$ M cytochrome c, $5\times10^{-5}$ M xanthin, $10^{-8}$ M xanthin oxidase. (A): open circles, $D_7(Ac^{115}, CuCl_2) \cdot 199H_2O$ ($2.48\times10^{-6}$M); filled circles, $D_7(Ac^{115}, PEG^{13}, CuCl_2) \cdot 210H_2O$ ($1.07\times10^{31\ 6}$ M); (B): open circles, $D_8(Ac^{226}, CuCl_2) \cdot 384H_2O$ ($1.10\times10^{-6}$ M); filled circles, $D_8(Ac^{226}, PEG^{30}, CuCl_2) \cdot 400H_2O$ ($0.70\times10^{-6}$ M).
Figure 8A:
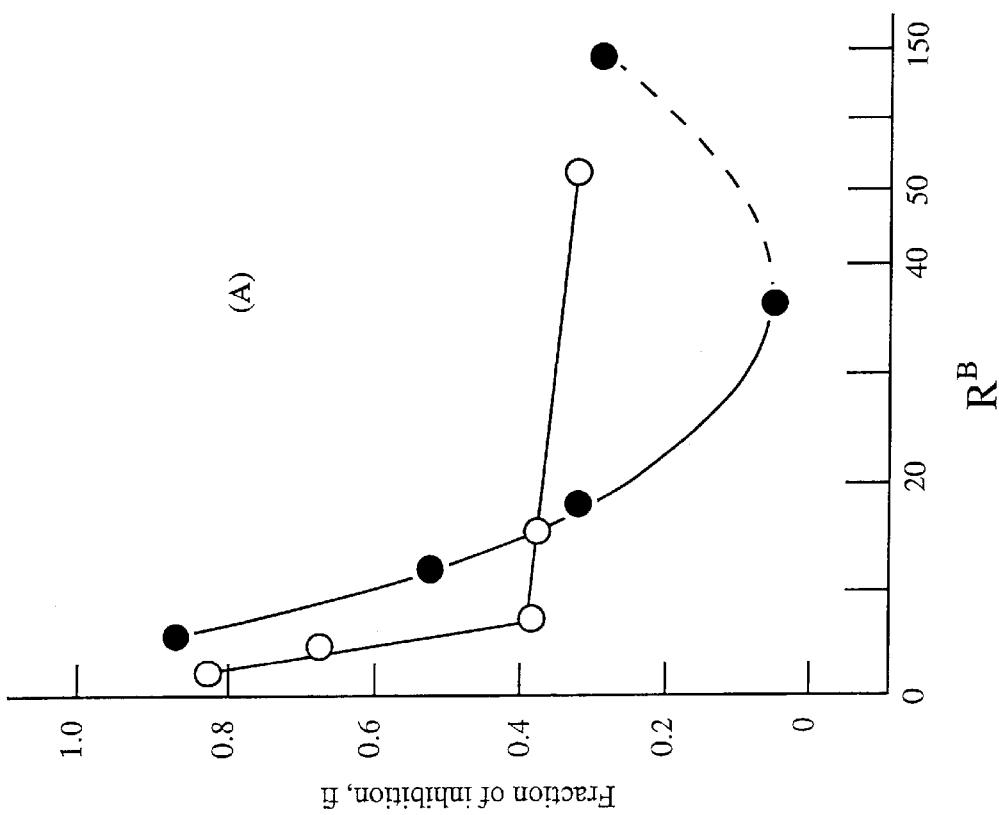

As shown in FIG. 8 and Table VII, the activity of acetylated D$_7$ rapidly decreased on increasing the molar ratio ($R^B$) of BSA to dendrimer from 0 to 8 reaching $f_i$=0.40 with $R^B_{50}$ (at $f_i$=0.50) of 6.7. The further increase of $R^B$, up to 50 where the concentration of BSA was 1%, further reduced the $f_i$ by only 0.08. The profile for glycolated D$_7$ was parabolic with $R^B_{50}$=13 and the minimum $f_i$ ($f_i^{min}$) at $R^B$=37. Thus, the fi increased to 0.30 on further increasing $R^B$ to 147 (1% BSA).

The parabolic profiles were also observed for D$_8$-dendrimers. The profile of acetylated D$_8$ was nearly identical to that of glycolated D$_7$ as expected in view of their being analogs. Glycolated D$_8$ had $R^B_{50}$=15, $f_i^{min}$=0.07 at $R^B$=56 and $f_i'$=0.14 at $R^B$=225 (1%). These results indicated that the $f_i^{min}$, occurred at higher $R^B$ with the higher generation dendrimer and further increase of $f_i$ was expected on increasing the BSA concentration above 1%. Reliable $f_i$ values were not obtained because of viscous and heterogeneous reaction mixtures of the test system.

The amino terminal fragment of BSA would be a candidate causal agent for the deterioration of the activity because it binds Cu$^{2+}$relatively strongly. On assuming a free access of BSA to the active site in the dendrimer, then a monotonous decrease of activity should be expected as in the case for EDTA. This was not the case and the direct interaction of BSA with the active site is unlikely. A plausible explanation for the parabolic feature of $f_i$ is as follows. The tiers consisting of amino acid residues would have affinity to some fragments of BSA and such fragments may penetrate inside the dendrimer molecule against steric interference due to the branched networks of tiers.

Use.

The metal ion-dendrimer complexes according to the invention can be administered in a suitable pharmaceutical medium for treatment of any of a variety of disease conditions associated with oxidative stress.

The complexes of the invention can be combined in a pharmacologically acceptable carrier suited for the desired mode of administration. For example the complex may be compounded as a gel or cream or ointment or liquid, for topical administration as for example on the skin or on a mucosal surface; or it may be suspended in a liquid carrier suitable for infusion or injection, for subcutaneous, intravenous, intraperitoneal, or intramuscular administration; or it may be compounded with a carrier as a liquid or dry powder for inhalation using a propellant or aerosol method.

Particularly, for example, a complex of the invention can be administered for treatment of intestinal damage associated with oxidative stress, such as duodenal and intestinal injury that develops in the course of endotoxemia or gastrointestinal damage resulting from chemotherapies or radiation therapies employed for cancer treatment. So-called SOD mimics are reported to be effective in such treatment (see, e.g., D. Salvemini et al 1999, *Science*, Vol. 286, pp. 305 ff.

And, for example, a complex of the invention can be administered for prophylaxis against inflammation or reperfusion injury associated with oxidative stress. Treatment for ischaemia-reperfusion injury is reported to be effective using SOD mimics (see, e.g., D. Salvemini et al. 1999, *Science*, vol. 286(5438), pages 209–210), or modified SODs (see, e.g., S. Kawasaki et al. 1993, *Eur. Surg. Res.*, vol. 25(3), pages 129 ff.; Y. Oyanagui 1989, *Rinsho Byori*, Vol. 37(9), pages 999 ff.; R. Ferrari et al. 1989, *Pharmacol. Res.*, vol. 21 suppl. 2, pages 57 ff.), or bovine SOD (see, e.g., G. Jadot et al. 1995, *Clin. Pharmacokinet.*, Vol. 28(1), pages 17 ff.), or recombnant SOD (see, e.g., T. Shibata et al. 1993).

And, for example, a complex of the invention can be used for prophylaxis against radiation-induced skin irritation or radiation-induced fibrosis. Liposomal SOD is reported to be effect in prophylactic treatment for UV-induced skin irritation (see, e.g., Y. Miyachi et at 1987, *Jour. Invest Dermatol.*, Vol. 89(1), pages 111–12), and for radiation-induced fibrosis (see, e.g., B. Perdereau et at 1994, *Bull. Cancer (Paris)*, Vol. 81(8), pages 659–69.

Other oxidative-stress associated disease conditions for which treatment using SODs or SOD mimics may be effective are reviewed in, for example, B. Halliwell et al. 1999, *Free Radicals in Biology and Medicine*, 3d Ed., Oxford, see particularly, chapters 9 and 10. Y. Niwa 1987, *Clin. Free Radicals*, Vol. 1, pp 69–76 (in Japanese) reports effective treatment using a liposome-encapsulated bovine SOD in humans for Crohn's disease, Bechet's syndrome, Kawasaki disease, light-induced skin disease and burn to the skin.

Other embodiments are within the following claims.

What is claimed is:

1. A metal-dendrimer complex having superoxide dismutase-like activity, comprising a dendrimer construct having a globular shape defining a surface, and having at least one metal ion complexed at a metal ion binding site situated within the volume defined by the surface of the construct, sufficiently deeply to impede diffusion from the metal ion binding site to the milieu surrounding the dendrimer construct surface of any hydroxyl radical generated by reaction of superoxide radical at said metal ion binding site.

2. The metal-dendrimer complex of claim 1 wherein said metal ion is selected from the group consisting of ions of copper and iron.

3. The metal-dendrimer complex of claim 1 wherein said metal ion comprises copper (II) ion.

4. The metal-dendrimer complex of claim 1 wherein said metal ion comprises iron (III) ion.

5. The metal-dendrimer complex of claim 1 wherein said dendrimer construct comprises a dendritic polypeptide.

6. The metal-dendrimer construct of claim 1 wherein said dendrimer construct comprises a dendritic polyamidoamine.

7. A dendrimer construct comprising a core and a plurality of branched arms projecting outwardly from said core, said arms comprising internal branched units and terminal moieties, said terminal moieties constituting an outer surface of the dendrimer construct and a metal ion binding site associated with an internal branched unit in at least one of said arms.

8. The dendrimer construct of claim 7 wherein said metal ion binding site comprises a plurality of imidazole moieties.

9. The dendrimer construct of claim 7 wherein said core comprises a number of reactive moieties in the range 1–4.

10. The dendrimer construct of claim 7, comprising a number of said arms in the range 1–4.

11. The dendrimer construct of claim 7 wherein the internal branch units are 1→2 branching or 1→3 branching.

12. The dendrimer construct of claim 7, comprising a dendritic polypeptide.

13. The dendrimer construct of claim 7, comprising a dendritic polyamidoamine.

14. The dendrimer construct of claim 9 wherein said core includes at least two reactive moieties.

15. The dendrimer of claim 7 wherein said core comprises an alkylamine.

16. The dendrimer of claim 7 wherein said core comprises a cyclic amino compound.

17. The dendrimer of claim 14 wherein said core comprises a diaminoalkane.

18. The dendrimer of claim 7 wherein said arms comprise as internal branch units α-amino acids carrying functional groups R in the side chain, wherein R is selected from the group consisting of $(CH_2)_nNH_2$, where n=1–7 and $(CH_2)_nCOOH$, where n=1–7.

19. The dendrimer of claim 8 wherein said plurality of imidazole moieties comprise a $N^{Im}$ (1)-alkylated histidine.

20. The dendrimer of claim 19 wherein said $N^{Im}(1)$ alkylated histidine is selected from the group consisting of $N^{Im}(1)$-methyl histidine, $N^{Im}(1)$-ethyl histidine, $N^{Im}(1)$-normal propyl histidine, $N^{Im}(1)$-normal butyl histidine, $N^{Im}(1)$-hexyl histidine, $N^{Im}(1)$-octyl histidine.

21. A metal-dendrimer complex having superoxide dismutase activity, comprising a dendrimer construct of claim 7, complexed with a metal ion selected from the group consisting of copper and iron.

22. A dendrimer construct of claim 7, being surface modified by attachment of a moiety selected from the group consisting of an acyl moiety, a poly(ethylene)glycol, a peptide fragment.

23. A method for treating a disease condition associated with oxidative stress, comprising administering a metal-dendrimer complex of claim 1 to a subject in need of treatment, in a form and by a route of administration suitable for bringing the complex to the site of the condition.

* * * * *